United States Patent
Costanzo et al.

(10) Patent No.: US 9,308,265 B2
(45) Date of Patent: Apr. 12, 2016

(54) NANOPARTICLES OF CERIUM AND AMINO ACIDS

(71) Applicant: Cerion Enterprises, LLC, Rochester, NY (US)

(72) Inventors: Wendi Ann Costanzo, Webster, NY (US); Kenneth Joseph Reed, Brighton, NY (US); Bradford Michael Stadler, Brighton, NY (US)

(73) Assignee: CERION LLC, Rochester, NY (US)

( * ) Notice: Subject to any disclaimer, the term of this patent is extended or adjusted under 35 U.S.C. 154(b) by 0 days.

(21) Appl. No.: 13/864,620

(22) Filed: Apr. 17, 2013

(65) Prior Publication Data

US 2013/0273659 A1    Oct. 17, 2013

Related U.S. Application Data

(60) Provisional application No. 61/687,050, filed on Apr. 17, 2012.

(51) Int. Cl.

| | | |
|---|---|---|
| *A61K 51/00* | (2006.01) | |
| *C12N 15/00* | (2006.01) | |
| *A61K 31/00* | (2006.01) | |
| *A61K 47/18* | (2006.01) | |
| *A61K 33/24* | (2006.01) | |
| *A61K 31/7088* | (2006.01) | |
| *A61K 31/713* | (2006.01) | |
| *A61K 9/51* | (2006.01) | |
| *B22F 9/24* | (2006.01) | |
| *B22F 1/00* | (2006.01) | |
| *A61K 47/48* | (2006.01) | |
| *C12N 15/87* | (2006.01) | |
| *B82Y 30/00* | (2011.01) | |
| *C01F 17/00* | (2006.01) | |

(52) U.S. Cl.
CPC ............ *A61K 47/183* (2013.01); *A61K 9/5115* (2013.01); *A61K 9/5123* (2013.01); *A61K 9/5192* (2013.01); *A61K 31/7088* (2013.01); *A61K 31/713* (2013.01); *A61K 33/24* (2013.01); *A61K 47/48861* (2013.01); *B22F 1/0018* (2013.01); *B22F 1/0022* (2013.01); *B22F 9/24* (2013.01); *B82Y 30/00* (2013.01); *C01F 17/0043* (2013.01); *C12N 15/87* (2013.01); *C01P 2002/60* (2013.01); *C01P 2002/70* (2013.01); *C01P 2002/72* (2013.01); *C01P 2004/04* (2013.01); *C01P 2004/64* (2013.01); *C01P 2006/90* (2013.01)

(58) Field of Classification Search
CPC ............... C01P 2004/64; A61K 2800/413; A61K 2800/56; A61K 47/00; A61K 47/48861; C09G 1/02; C09G 1/04; B82Y 30/00; B01J 23/96; B01J 35/0013; B01J 35/006; C12N 2531/00; C12N 2533/20

See application file for complete search history.

(56) References Cited

U.S. PATENT DOCUMENTS

| | | | |
|---|---|---|---|
| 6,530,968 B2 * | 3/2003 | Tsuchiya et al. ............... | 51/307 |
| 7,534,453 B1 | 5/2009 | Rzigalinski et al. | |
| 2003/0082237 A1 * | 5/2003 | Cha et al. ...................... | 424/490 |
| 2003/0187077 A1 | 10/2003 | Chane-Ching | |
| 2006/0018851 A1 * | 1/2006 | Patt ................................ | 424/62 |
| 2010/0152077 A1 | 6/2010 | Allston et al. | |
| 2010/0221344 A1 * | 9/2010 | Seal et al. ..................... | 424/489 |
| 2010/0308258 A1 * | 12/2010 | Kroell .......................... | 252/79.1 |

FOREIGN PATENT DOCUMENTS

| | | |
|---|---|---|
| WO | WO 2007/002662 A2 | 1/2007 |
| WO | WO 2008/002323 A2 | 1/2008 |
| WO | WO 2008/030805 A1 | 3/2008 |
| WO | WO 2008/030815 A2 | 3/2008 |

OTHER PUBLICATIONS

Illustrated Glossary of Organic Chemistry. downloaded from http://www.chem.ucla.edu/harding/IGOC/A/amino_acid.html on Feb. 18, 2014.*
Material Safety and Data Sheet for Ethylenediaminetetraacetic acid from Sigma Aldrich, 2014.*
"Aliphatic Amino Acids", The Biology Project, 2004. downloaded from http://www.biology.arizona.edu/biochemistry/problem_sets/aa/aliphatic.html on Feb. 18, 2014.*
Zhang et al. Synthesis and Characterization of Mesoporous Ceria with Hierarchical Nanoarchitecture Controlled by Amino Acids. Journal of Physical Chemistry B, 2006. 110:25782-25790.*
Aryal et al. Study of Electrolyte Induced Aggregation of Gold Nanoparticles Capped by Amino Acids, Journal of Colloid and Interface Science. 2006. 299:191-197.*
Nitric Acid Material Safety Data Sheet, CF Industries Sales, LLC, 2012, 8 Pages.*
EPO, International Search Report of PCT/US2013/032318, Jun. 5, 2013.
Rzigalinski, Beverly A. Ph.D., "Nanoparticles and Cell Longevity," Technology in Cancer Research and Treatment, vol. 4, No. 6, pp. 651-659, Dec. 2005.
Masui, T. et al., "Synthesis of Cerium Oxide Nanoparticles by Hydrothermal Crystallization With Citric Acid," J. Mater. Sci. Lett. 21, pp. 489-491, 2002.
Hardas, Sarita et al., "Brain Distribution and Toxicological Evaluation of a Systemically Delivered Engineered Nanoscale Ceria," Toxicologial Sciences 116(2), pp. 562-576, 2010.
Karokoti, A.S. et al.; "Direct Synthesis of Nanoceria in Aqueous Polyhydroxyl Solutions," J. Physical Chem. C 111, pp. 17232-17240, 2007.

(Continued)

*Primary Examiner* — Christopher M Babic
*Assistant Examiner* — Kimberly A Aron
(74) *Attorney, Agent, or Firm* — RatnerPrestia

(57) ABSTRACT

A process for making nanoparticles of biocompatible materials is described, wherein an aqueous reaction mixture comprising cerous ion, an α-amino acid, an oxidant and water is provided along with temperature conditions to effectively form nanoparticles. These biocompatible nanoparticles may be further conjugated to biologically active agents, such as plasmid DNA, siRNA or proteins, such that a cell transfection agent is formed.

18 Claims, 10 Drawing Sheets

(56) References Cited

OTHER PUBLICATIONS

Karokoti, A.S. et al., "Nanoceria as Antioxidant: Systhesis and Biomedical Applications," Journal of the Minerals, Metals & Materials Society (JOM), 60(2), pp. 33-37, Mar. 2008.

Kim, Chi Kyung et al., "Ceria Nanoparticles That Can Protect Against Ischemic Stroke", Angew. Chem. Int., vol. 6, pp. 1-6, Ed. 2012.

Estevez, A.Y. et al., "Neuroprotective Mechanisms of Cerium Oxide Nanoparticles in a Mouse Hippocampal Brain Slice Model of Ischemia," Free Radic. Biol. Med, 2011, doi : 10.1016/j.freeradbiomed.2011.06.006.

"Metallic Nanocrystallites and Their Interaction With Microbial Systems"; Springer, XP002697256, Mar. 2, 2012.

Robert A. Yokel et al. "Biodistribution and Oxidative Stress Effects of a Systemically-Introduced Commercial Ceria Engineered Nanomaterial," Nanotoxicology, vol. 3, pp. 234-248, Sep. 2009.

EPO; International Search Report of PCT/US2013/036943; Oct. 11, 2013.

Notice of Allowance Issued to U.S. Appl. No. 13/836,827, Dated Mar. 18, 2015.

Entire Prosecution History for U.S. Appl. 13/836,827, filed Mar. 15, 2013, Entittled " Nanoceria for the Treatment of Oxidative Stress".

Garrett, "Some Common Crystal Structures" 1998.

* cited by examiner

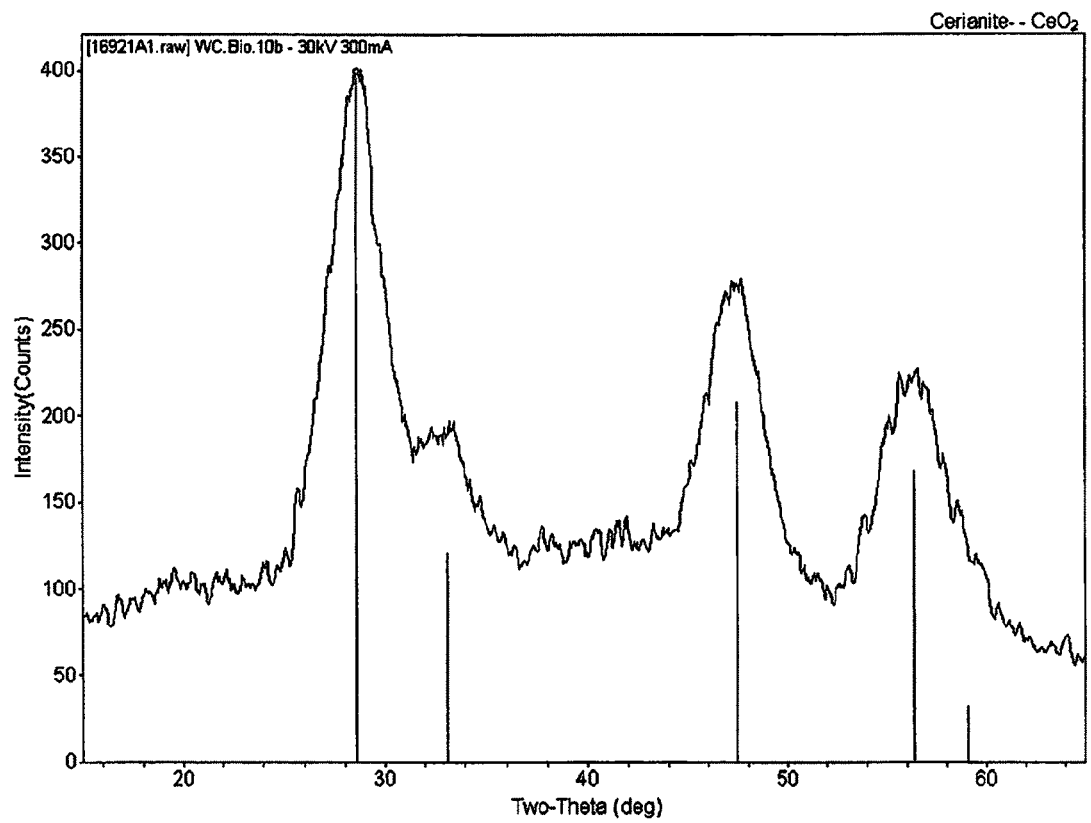
FIG. 1: XRD Spectrum of Nanoparticles Prepared with 0.8/1.0 Arginine/Cerium

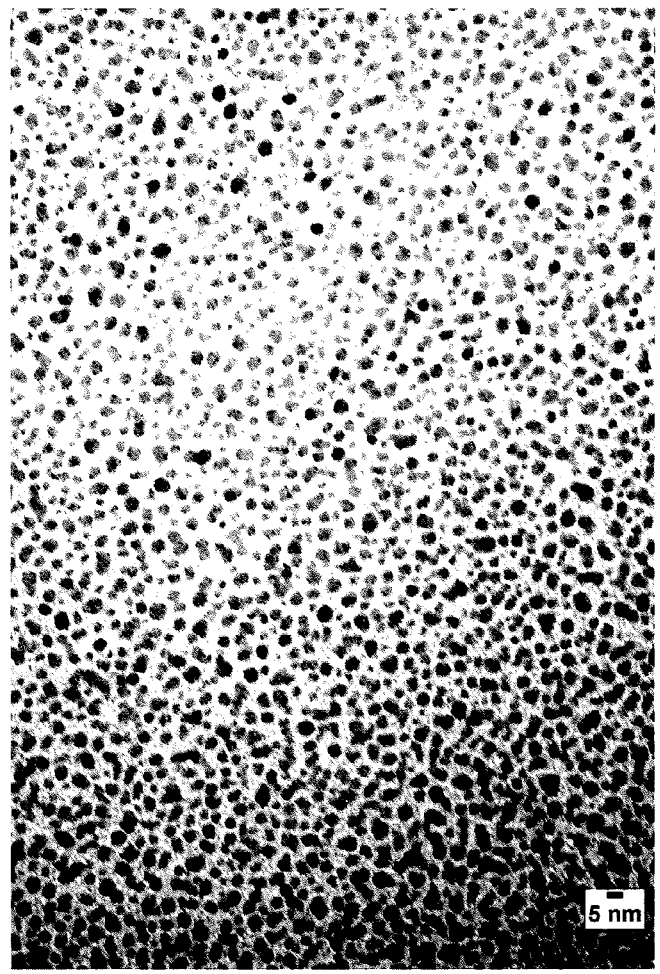
FIG. 2: TEM image of the particles prepared with 1/1 Arginine/Cerium

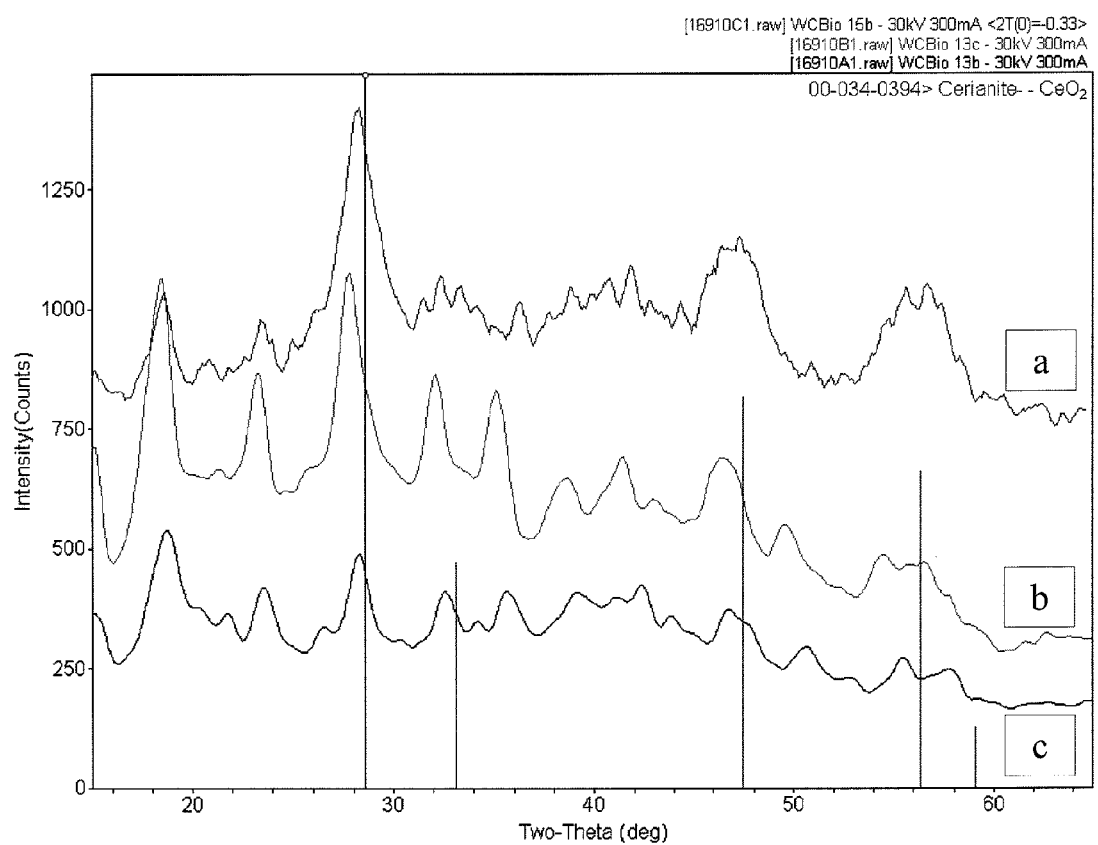
FIG. 3: XRD spectra of nanoparticles prepared in Histidine/Cerium (spectrum a), and Lysine/Cerium (spectrum b, spectrum c)

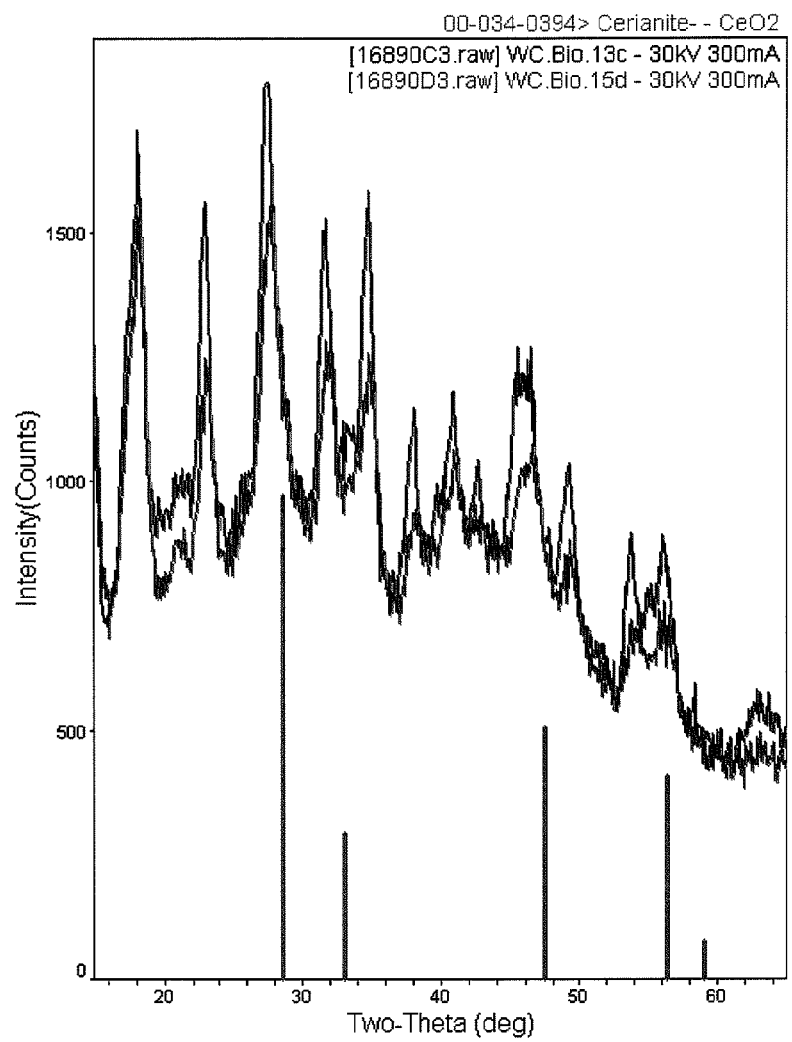
FIG. 4: XRD Spectra of Nanoparticles Prepared with a 1.2 molar ratio of Histidine/Cerium and with a 1.2 molar ratio of Lysine/Cerium

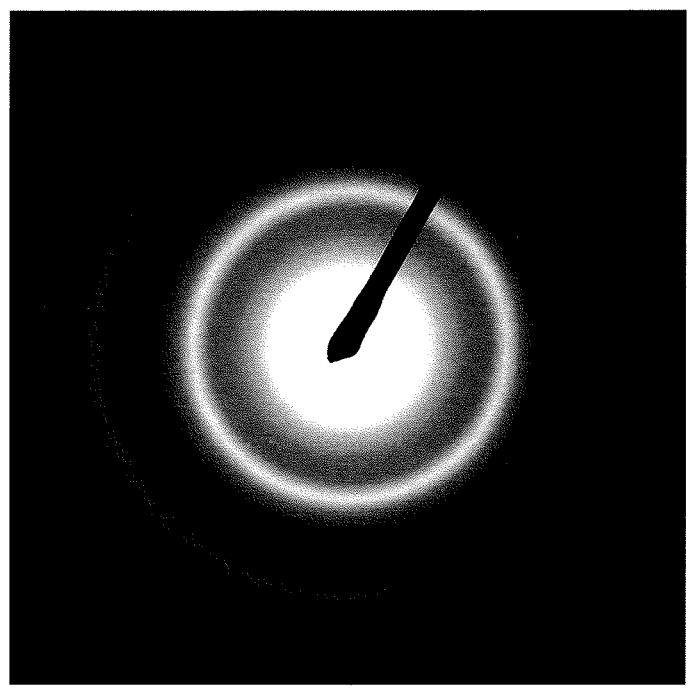
FIG. 5: Electron diffraction pattern of nanoparticles prepared in (0.9/0.1) Arginine/Histidine

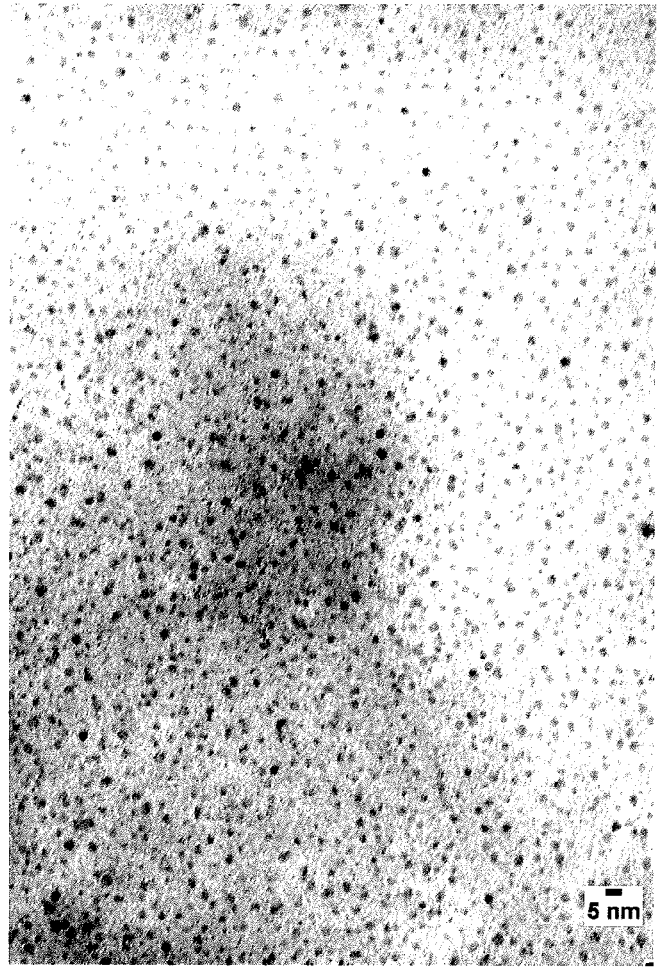
FIG. 6: TEM image of the nanoparticles prepared in a (0.9/0.1) mixture of Arginine/Histidine

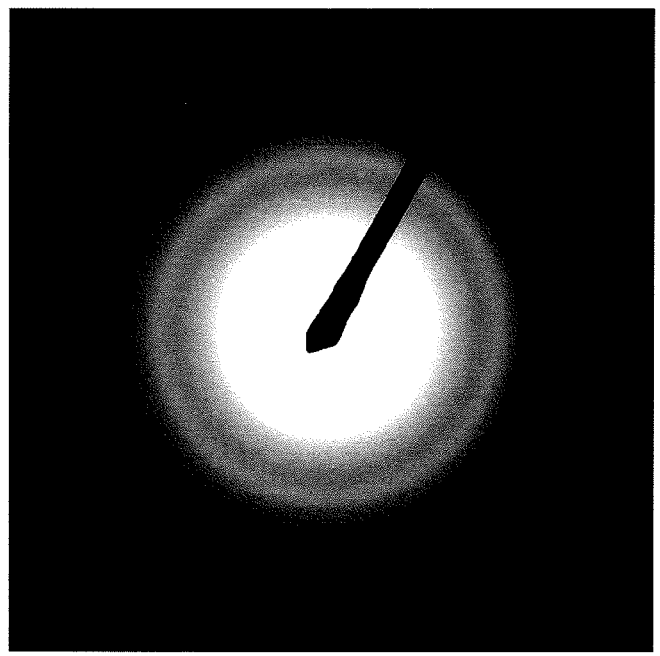
FIG. 7: Electron diffraction pattern of nanoparticles prepared in a (0.7/0.3) mixture of Arginine/Histidine

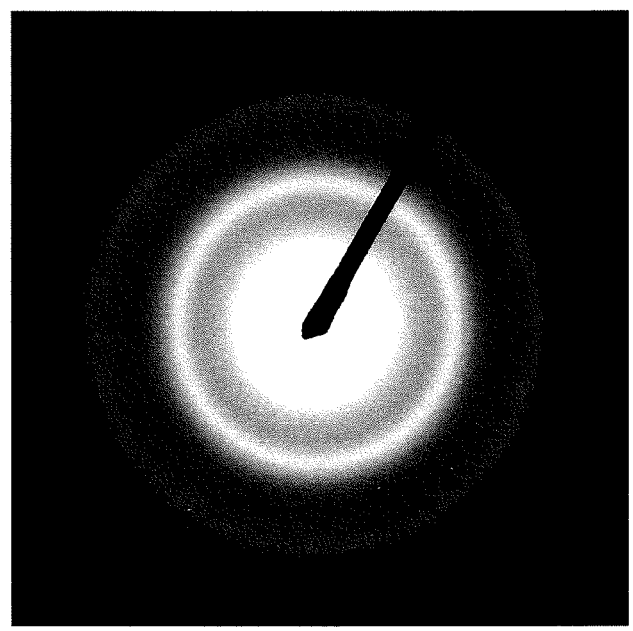
FIG. 8: Electron diffraction pattern of nanoparticles prepared in a (0.5/0.5) mixture of Arginine/Histidine

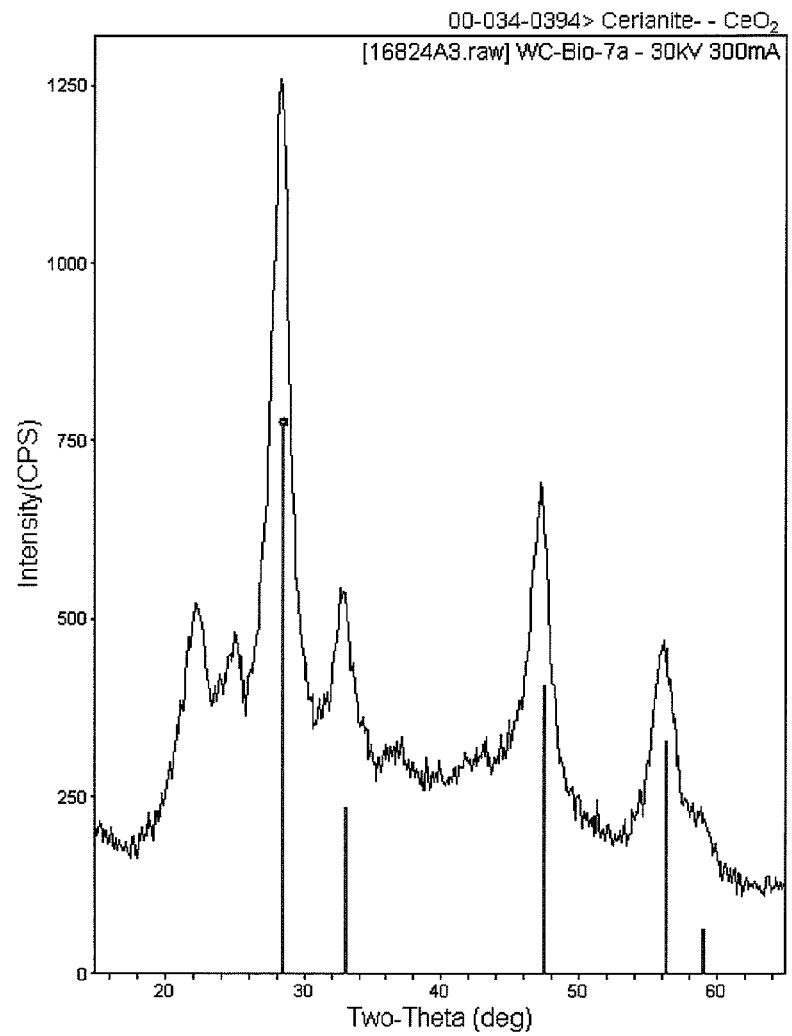
FIG. 9: XRD Spectrum of Nanoparticles Prepared with a 3.2 molar ratio of Alanine/Cerium

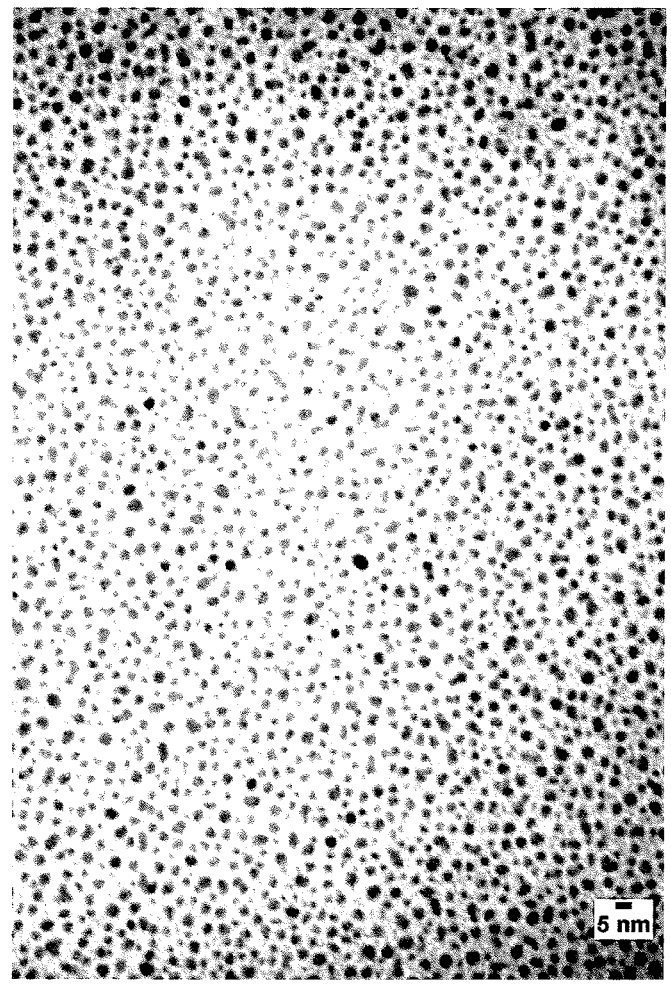
FIG. 10: TEM image of the nanoparticles prepared with a 0.8 molar ratio of Isoleucine/Cerium

NANOPARTICLES OF CERIUM AND AMINO ACIDS

CROSS-REFERENCE TO RELATED APPLICATIONS

This patent application claims priority to Provisional Patent Application Ser. No. 61/687,050, NANOPARTICLES PREPARED WITH CERIUM AND AMINO ACIDS, filed Apr. 17, 2012, the disclose of which is incorporated herein by reference in its entirety.

FIELD OF THE INVENTION

The present invention relates in general to improvements in the field of nanomedicine. In particular, the invention relates to nanoparticles prepared with biocompatible materials, to methods of preparing such nanoparticles, to conjugates of such nanoparticles with biological agents, and to the use of such nanoparticles or conjugates thereof to treat disease, to reduce complications due to inflammation, radiation exposure and aging, to transfect cells or to deliver drugs.

BACKGROUND OF THE INVENTION

The origin of the use of nanoceria in nanomedicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, *Technology in Cancer Research & Treatment* 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as disclosed by Rzigalinski et al. in U.S. Pat. No. 7,534,453, filed Sep. 4, 2003. Cultured brain cells exposed to a lethal dose of free radicals generated by hydrogen peroxide or ultraviolet light exposures were afforded considerable protection by the cerium oxide nanoparticles. In addition, the cerium oxide nanoparticles were reported to be relatively inert in the murine body, with low toxicity (e.g. tail vein injections produced no toxic effects). While no in vivo medical benefits were reported, benefits were postulated for treatments with these ceria nanoparticles, including reduced inflammation associated with wounds, implants, arthritis, joint disease, vascular disease, tissue aging, stroke and traumatic brain injury.

However, a host of problems with these particular nanoceria particles was subsequently disclosed by Rzigalinski et al. in WO 2007/002662. Nanoceria produced by this reverse micelle micro emulsion technique suffered from several problems: (1) particle size was not well-controlled within the reported 2-10 nanometer (nm) range, making variability between batches high; (2) tailing of surfactants, such as sodium bis(ethylhexyl)sulphosuccinate, also known as docusate sodium or (AOT), used in the process into the final product caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 describe the biological efficacy of nanoceria synthesized by high temperature techniques, obtained from at least three commercial sources. These new sources of cerium oxide nanoparticles were reported to provide superior reproducibility of activity from batch to batch. It was further reported that, regardless of source, cerium oxide particles having a small size, narrow size distribution, and low agglomeration rate are most advantageous. In regard to size, this disclosure specifically teaches that in embodiments where particles are taken into the interior of cells, the preferable size range of particles that are taken into the cell are from about 11 nm to about 50 nm, such as about 20 nm. In embodiments where particles exert their effects on cells from outside the cells, the preferable size range of these extracellular particles is from about 11 nm to about 500 nm.

These inventors (Rzigalinski et al.) also report that for delivery, the nanoparticles were advantageously in a non-agglomerated form. To accomplish this, they reported that stock solutions of about 10% by weight could be sonicated in ultra-high purity water or in normal saline prepared with ultra-high purity water. We have observed, however, that sonicated aqueous dispersions of nanoceria (synthesized by high temperature techniques and obtained from commercial sources) are highly unstable, and settle rapidly (i.e. within minutes), causing substantial variability in administering aqueous dispersions of nanoceria derived from these sources.

These inventors (Rzigalinski et al.) report biological efficacy in relatively simple model systems, including in vitro cell cultures, orally fed *Drosophila melanogaster* fruit flies, and in mice that were tail vein injected with a relatively low dose (300 nanomoles or about 0.2 mg/kg).

Yokel et al. in *Nanotoxicology*, 2009, 3(3): 234-248, describe an extensive study of the biodistribution and oxidative stress effects of a commercial ceria nanomaterial. In particular, a 5% nanoceria dispersion obtained from Aldrich (#639648) was sonicated for 3 minutes and infused into rats at 50, 250 and 750 mg/kg nanoceria dose. The nature of any nanoparticle surface stabilizer(s) was unknown for this material. The size of the nanoceria particles was characterized by a variety of techniques and reported to be on average 31+/−4 nm by dynamic light scattering. Transmission electron microscopy (TEM) revealed that most of the particles were platelets with a bimodal size distribution with peaks at 8 nm and 24 nm, along with some particles ~100 nm. It was observed that blood incubated for 1 hour with this form of nanoceria had agglomerates ranging from ~200 nm to greater than 1 micron, and that when infused into rats, it was rapidly cleared from the blood (half-life of 7.5 minutes). Most of the nanoceria was observed to accumulate in the liver and spleen, while it was not clear that any substantial amount had penetrated the blood brain barrier and entered brain tissue cells.

This group of authors then sought precise control over the nanoceria surface coating (stabilizer) and prepared stable aqueous dispersions of nanoceria by the direct two-step hydrothermal preparation of Masui et al., *J. Mater. Sci. Lett.* 21, 489-491 (2002), which included sodium citrate as a biocompatible stabilizer. High resolution TEM revealed that this form of nanoceria possessed crystalline polyhedral particle morphology with sharp edges and a narrow size distribution of 4-6 nm. Citrate stabilized dispersions of these 5 nm average ceria nanoparticles were reported to be stable for more than 2 months at a physiological pH of 7.35 and zeta potential of −53 mV. Thus no sonication prior to administration was required.

Results of an extensive biodistribution and toxicology study of this form of citrate stabilized nanoceria was reported by this group of authors in Hardas et al., *Toxicological Sci-* ences 116(2), 562-576 (2010). Surprisingly, they report that compared with the previously studied ~30 nm nanoceria (Aldrich (#639648) described above), this nanoceria was more toxic, was not seen in the brain, and produced little oxidative stress effect to the hippocampus and cerebellum. The results were contrary to the hypothesis that smaller engineered nanomaterial would readily permeate the blood brain barrier.

While cerium oxide containing nanoparticles can be prepared by a variety of techniques known in the art, the particles typically require a stabilizer to prevent undesirable agglomeration. In regard to biocompatible nanoceria stabilizers used previously, once again, Masui et al., *J. Mater. Sci. Lett.* 21, 489-491 (2002) describe a two-step hydrothermal process that directly produces stable aqueous dispersions of ceria nanoparticles that use citrate buffer as a stabilizer. However, this process is both time and equipment intensive, requiring two separate 24 hours reaction steps in closed reactors.

Sandford et al., WO 2008/002323 A2, describe an aqueous preparation technique using a biocompatible stabilizer (acetic acid) that directly produces nanoparticle dispersions of cerium dioxide without precipitation and subsequent calcination. Cerous ion is slowly oxidized to ceric ion by nitrate ion, and a stable non-agglomerated sol of 11 nm crystallite size (and approximately equal grain size) is obtained when acetic acid is used as a stabilizer.

DiFrancesco et al. in PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible stabilizers, such as citric acid, lactic acid, tartaric acid, malic acid, ethylenediaminetetraacetic acid (EDTA), and combinations thereof. Specifically, the stabilizer lactic acid and the combination of lactic acid and EDTA are shown to directly produce stable dispersions of nanoceria of average particle size in the range of 3-8 nm, which have subsequently been shown to have negative zeta potentials.

Karakoti et al. in *J. Phys. Chem. C* 111, 17232-17240 (2007) describe the direct synthesis of nanoceria in mono/polysaccharides by oxidation of cerous ion in both acidic conditions (by hydrogen peroxide) and basic conditions (by ammonium hydroxide). The specific biocompatible stabilizers disclosed include glucose and dextran. Individual particle sizes as small as 3-5 nm are disclosed, however, weak agglomerates of 10-30 nm resulted. While the source of the colloidal instability is not described, we speculate that the magnitude zeta potential of these particles may not have been sufficiently large.

Karakoti et al. in JOM (Journal of the Minerals, Metals & Materials Society) 60(3), 33-37 (2008) comment on the challenge of synthesizing stable dispersions of nanoceria in biologically relevant media, so as to be compatible with organism physiology, as requiring an understanding of colloidal chemistry (zeta potential, particle size, dispersant, pH of solution, etc.) so as not to interfere with the reduction/oxidation (redox) ability of the nanoceria that enables the scavenging of free radicals (reactive oxygen species (ROS) and reactive nitrogen species). These authors specifically describe the oxidation of cerium nitrate by hydrogen peroxide at low pH (<3.5) in the absence of any stabilizer, as well as, in the presence of dextran, ethylene glycol and polyethylene glycol (PEG) stabilizers. Particle sizes of 3-5 nm are reported, although particle agglomeration to 10-20 nm is also disclosed.

The term transfection refers to a process of deliberately introducing nucleic acids into cells. However, currently available techniques for transfecting a cell are greatly limited in their ability to efficiently introduce nucleic acids into cells for the study of gene function (e.g. overexpression of genes by plasmid or gene silencing via small RNAs). The state of the art techniques in use today also suffer from issues with cytotoxicity, inefficient delivery to cells, or inability to transfect a wide range of cell lines.

As described above, various methods and apparatus have been reported for preparing dispersions of cerium-containing nanoparticles. However, a need remains for further improvements in methods for the direct preparation of biocompatible dispersions of nanoparticles, for example, without isolation of the nanoparticles, in higher yield, in a shorter period of time and at higher suspension densities, that are sufficiently small in size (less than about 4 nm in mean geometric diameter), uniform in size frequency distribution, stable and non-toxic in a wide range of biological media. Additionally, it would be quite useful to produce these nanoparticles and conjugates thereof with positive zeta potentials whose magnitude could be varied at will over a relatively large range. Finally, it would be very desirable to produce biocompatible stabilized nanoparticles that can effectively form conjugates with other biologically active agents, such as, for example, peptides/proteins, various DNA and RNA species, for use as drugs, vaccines or transfection agents.

SUMMARY OF THE INVENTION

In accordance with a first aspect the invention, a process of making a dispersion of nanoparticles is provided, comprising: forming a reaction mixture comprising cerous ion, an α-amino acid, an oxidant, and water; optionally, heating or cooling the reaction mixture; and forming a dispersion of nanoparticles from the reaction mixture.

In a second aspect of the invention, a process of making a dispersion of nanoparticles is provided, comprising: forming a reaction mixture comprising cerous ion, an α-amino acid, an oxidant, and water; adjusting the pH of the reaction mixture to less than about 3, optionally, heating or cooling the reaction mixture, and thereby forming a dispersion of nanoparticles, is provided.

In a third aspect of the invention, a nanoparticle comprising an α-amino acid and a metal is provided.

In a fourth aspect of the invention, a nanoparticle comprising an α-amino acid and cerium is provided.

In a fifth aspect of the invention, a crystalline nanoparticle comprising an α-amino acid and cerium is provided.

In a sixth aspect of the invention, a nanoparticle comprising an α-amino acid and cerium, and further characterized by a zeta potential greater than zero, is provided.

In a seventh aspect of the invention, a process of making a conjugate, comprising: contacting a cerium-containing nanoparticle comprising an α-amino acid and a metal, with a biologically active agent, is provided.

In an eighth aspect of the invention, a conjugate comprising: a cerium oxide nanoparticle comprising an α-amino acid, a metal, and a biologically active agent comprising a ribonucleic acid, deoxyribonucleic acid or protein, is provided.

In an ninth aspect of the invention, a conjugate comprising: a cerium oxide nanoparticle comprising an α-amino acid, a metal, and a biologically active agent comprising siRNA, miRNA, an aptamer/riboswitch, plasmid DNA or epitope, is provided.

In a tenth aspect of the invention, a conjugate comprising: a cerium-containing nanoparticle comprising an α-amino acid, a metal, and a biologically active agent, is used as a cell transfection agent.

In aspect of the invention, a conjugate comprising: a nanoparticle of an α-amino acid, cerium or a cerium oxide, and a biologically active agent, is used as a vaccine or drug delivery vehicle.

In an eleventh aspect of the invention, a process of transfecting a cell, comprising: contacting a cell with a conjugate comprising; (1) a cerium-containing nanoparticle comprising an α-amino acid, and (2) a biologically active agent, is provided.

BRIEF DESCRIPTION OF THE DRAWINGS

FIG. 1 is a powder X-ray Diffraction (XRD) spectrum of the nanoparticles prepared in Example 1d, along with the line spectrum of $CeO_2$ (Cerianite).

FIG. 2 is a transmission electron microscopy (TEM) image representative of the particles prepared in Example 1e.

FIG. 3 contains powder X-ray Diffraction (XRD) spectra of the nanoparticles prepared in Example 2a (0.4 molar ratio of histidine/cerium) (see spectrum a), Example 4b (0.8 molar ratio of lysine/cerium) (see spectrum c), and Example 4c (1.2 molar ratio of lysine/cerium) (see spectrum b), along with the line spectrum of $CeO_2$ (Cerianite).

FIG. 4 contains powder XRD spectra of the nanoparticles prepared in Example 2c (1.2 molar ratio of histidine/cerium) and Example 4c (1.2 molar ratio of lysine/cerium), along with the line spectrum of $CeO_2$ (Cerianite).

FIG. 5 is an electron diffraction pattern of the particles prepared in Example 3i.

FIG. 6 is a TEM image representative of the particles prepared in Example 3i.

FIG. 7 is an electron diffraction pattern of the particles prepared in Example 3j.

FIG. 8 is an electron diffraction pattern of the particles prepared in Example 3k.

FIG. 9 is an XRD spectrum of nanoparticles prepared in Example 8b (3.2 molar ratio of alanine/cerium).

FIG. 10 is a TEM image representative of the particles prepared in Example 11.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its hydrodynamic diameter, which is the diameter determined by dynamic light scattering technique and includes molecular adsorbates and the accompanying solvation shell of the particle. Alternatively, the geometric particle diameter can be estimated by analysis of transmission electron micrographs (TEM).

In this application, the term α-amino acid (alpha-amino acid) refers to a molecule comprised of an amine group, a carboxylic acid group and a side chain (R), wherein the amine group and the side chain are attached to the carbon atom immediately adjacent to the carboxyl group. An α-amino acid has the generic formula $H_2NCHRCOOH$.

In this application, various cerium-containing materials are nominally described as "cerium oxide" or "cerium dioxide." It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for oxide phases comprised of metal cations of multiple oxidation states, it is understood that the total amount of oxidic anions present will be determined by the specific amounts of the various oxidation states of the metal cations present (e.g. $Ce^{3+}$ and $Ce^{4+}$), such that charge neutrality is maintained. For non-stoichiometric phases nominally described as metal dioxides, this is embodied in the chemical formula $MO_{2-\delta}$ wherein the value of δ (delta) may vary. For a cerium oxide, $CeO_{2-\delta}$, the value of δ (delta) typically ranges from about 0.0 to about 0.5, the former denoting cerium (IV) oxide, $CeO_2$, the latter denoting cerium (III) oxide, $CeO_{1.5}$ (alternatively denoted $Ce_2O_3$).

In one aspect of the invention, a process is provided comprising: forming a reaction mixture comprising cerous ion, an α-amino acid, an oxidant, and water; optionally heating or cooling the reaction mixture; and forming a dispersion of nanoparticles from the reaction mixture.

In a particular embodiment, an additional process step of adjusting the pH of the reaction mixture to less than 5, less than 4, less than 3 or less than about 2, is provided.

In particular embodiments, the α-amino acid is a biocompatible material.

In particular embodiments, the α-amino acid contains a side chain that is positively charged at physiological pH, such as arginine, histidine or lysine.

In particular embodiments, the α-amino acid contains a side chain that is uncharged at physiological pH, such as serine, threonine, asparagine or glutamine.

In particular embodiments, the α-amino acid contains a side chain that is negatively charged at physiological pH, such as aspartic acid or glutamic acid.

In particular embodiments, the α-amino acid contains a side chain that is hydrophobic, such as alanine, valine, isoleucine, leucine, methionine, phenylalanine, tyrosine or tryptophan.

In particular embodiments, the α-amino acid is cysteine, selenocysteine, glycine or proline.

In a particular embodiment, a mixture of α-amino acids is employed, such as, but not limited to, arginine and histidine, arginine and serine, and arginine and isoleucine.

Physiological pH is generally in the range of about 7.2 to about 7.4.

In various embodiments, the oxidant includes compounds more oxidizing than molecular oxygen (or an ambient atmosphere of air). In other embodiments, the oxidant has an aqueous half-cell reduction potential greater than −0.13 volts relative to the standard hydrogen electrode. In particular embodiments the oxidant is an alkali metal or ammonium perchlorate, chlorate, hypochlorite or persulfate; ozone, a peroxide or a combination thereof. In a particular embodiment, a two-electron oxidant, such as hydrogen peroxide, is used. In particular embodiments, hydrogen peroxide is present in an amount greater than one-half the molar amount of cerous ion. In still other embodiments, the amount of oxidant present varies widely in relation to the amount of cerium ions or other metal ions present.

In a particular embodiment, molecular oxygen is passed through the reaction mixture.

In particular embodiments, the temperature of the reaction mixture is greater than or less than ambient temperature. In particular embodiments, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C.

In various embodiments, the nanoparticles formed are amorphous, semi-crystalline or crystalline. In particular embodiments the nanoparticles formed are characterized by a cubic fluorite crystal structure. In a particular embodiment, the nanoparticles formed are characterized by a cerium oxide crystal structure.

In particular embodiments, the nanoparticles formed are characterized by a powder XRD peak position ranging from 7-10 degrees Two-Theta, from 13-16 degrees Two-Theta, from 17-19 degrees Two-Theta, from 22-24 degrees Two-Theta, from 26-29 degrees Two-Theta, from 30-32 degrees Two-Theta, from 34-36 degrees Two-Theta, from 39-41 degrees Two-Theta, from 42-43 degrees Two-Theta, from 45-47 degrees Two-Theta, from 48-50 degrees Two-Theta, from 53-54 degrees Two-Theta or from 55-57 degrees Two-Theta.

In particular embodiments, the crystallinity of the nanoparticles formed is enhanced by heating of the reaction mixture.

In particular embodiments, the nanoparticles formed are dehydrated, dehydroxylated or deprotonated by heating of the reaction mixture.

In particular embodiments, the reaction mixture further comprises metal ions other than cerium ions, such as gold, platinum or palladium ions. In particular embodiments, a transition metal or a rare earth metal is incorporated into the interior or on the surface of the nanoparticle. In other embodiments, the transition or rare earth metal ion is substituted for a cerium ion and thereby occupies a cerium ion site in a crystalline or amorphous nanoparticle.

In various embodiments, the transition or rare earth metal ion may be introduced into the reaction mixture prior to, concurrently with, or after the addition of the cerous ion.

In particular embodiments, the nanoparticles formed contain surface metal ions capable of bonding to a ligand molecule, such as an α-amino acid.

In various embodiments, the nanoparticles formed have a hydrodynamic diameter less than 100 nm, less than 80 nm, less than 60 nm, less than 40 nm, less than 20 nm, less than 10 nm, less than 5.0 nm or less than about 2.0 nm.

In a particular embodiment of the invention, a nanoparticle comprising an α-amino acid and a metal is provided.

In particular embodiments, the metal may comprise cerium, gold, platinum or palladium. In particular embodiments, the nanoparticle may comprise a transition metal or a rare earth metal. In particular embodiments, the nanoparticle may comprise more than one metal.

In a particular embodiment, a nanoparticle comprising an α-amino acid and cerium is provided.

In a particular embodiment, a nanoparticle comprising cerium is provided. In other embodiments, nanoparticles comprising a cerium oxide, a cerium hydroxide or a cerium oxyhydroxide are provided.

In a particular embodiment, a nanoparticle comprising an α-amino acid and a cerium oxide, cerium hydroxide or cerium oxyhydroxide, is provided.

In particular embodiments, a nanoparticle having a zeta potential greater than zero is provided. In particular embodiments, a nanoparticle comprising an α-amino acid and having a zeta potential greater than zero is provided. In particular embodiments, a nanoparticle comprising an α-amino acid, optionally cerium, and having a zeta potential greater than zero, greater than 10 mV, greater than 20 mV, greater than 30 mV, greater than 40 mV or greater than 50 mV, is provided.

In other embodiments, a nanoparticle having a zeta potential less than or equal to zero is provided. In particular embodiments, a nanoparticle comprising an α-amino acid and having a zeta potential less than or equal to zero is provided. In particular embodiments, a nanoparticle comprising an α-amino acid, optionally cerium, and having a zeta potential less than −10 my, less than −20 mV, less than −30 my, less than −40 mV or less than about −50 mV, is provided.

In various embodiments, the zeta potential of the nanoparticle is altered by adjusting the pH, the α-amino acid content, or a combination thereof, of the nanoparticle dispersion.

In a particular embodiment, the zeta potential of the nanoparticle is altered by adjusting the α-amino acid content of the nanoparticle dispersion to less than saturation coverage.

In another embodiment, the zeta potential of the nanoparticle is altered by adjusting both the pH of the nanoparticle dispersion, and the α-amino acid content to less than saturation coverage.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed without isolation of the nanoparticles, such as, for example, by dialysis or diafiltration, thereby maintaining a stable nanoparticle dispersion.

In particular embodiments, the nanoparticle dispersions formed are concentrated to remove excess solvent or excess water. In particular embodiments, the nanoparticle dispersion is concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distributions of the nanoparticles are substantially monomodal. In other embodiments, the nanoparticle size has a coefficient of variation (COV) less than about 30%, less than about 25%, less than about 20%, less than about 15%, less than about 10% or less than about 5%, where the COV is defined as the standard deviation divided by the mean.

In various embodiments, the reaction mixture is formed in a batch reactor, a continuous reactor or a colloid mill. In particular embodiments, the continuous reactor is a continuous-stirred-tank reactor or a plug-flow reactor.

In particular embodiments, mixers can be used to agitate and mix the reactants. In various embodiments, mixers comprising stir bars, marine blade propellers, pitch blade turbines or flat blade turbines are used. In a particular embodiment, a high shear mixer that forces the reaction mixture to pass through a screen, wherein holes vary in size from fractions of a millimeter to several millimeters, is employed.

In one embodiment of the invention, a process of solvent shifting the aqueous nanoparticle dispersion to a less polar solvent composition by methods disclosed in commonly assigned US Patent Application Publication 2010/0152077, is employed. In a specific embodiment, the nanoparticle dispersion is passed through a diafiltration column with an organic diluent. In a specific embodiment, the organic diluent comprises one or more alcohols or glycol ethers.

In a particular embodiment of the invention, a conjugate comprising (1) a nanoparticle comprising an α-amino acid and a metal, and (2) a biologically active agent is provided. In particular embodiments, the metal is cerium, gold, platinum, palladium, a transition metal, a rare earth metal, or combination thereof.

In a particular embodiment, a conjugate comprising (1) a nanoparticle comprising an α-amino acid and cerium, and (2) a biologically active agent is provided.

In a particular embodiment, a conjugate comprising (1) a nanoparticle comprising an α-amino acid and a cerium oxide, and (2) a biologically active agent is provided.

In various embodiments, a conjugate comprising (1) a nanoparticle comprising an α-amino acid, and (2) a biologically active agent comprising a ribonucleic acid, a deoxyribonucleic acid or a protein is provided.

In other various embodiments, a conjugate comprising (1) a nanoparticle comprising an α-amino acid and cerium, and (2) a biologically active agent comprising a ribonucleic acid, a deoxyribonucleic acid or a protein is provided.

In still other various embodiments, a conjugate comprising (1) a nanoparticle comprising an α-amino acid and a cerium oxide, and (2) a biologically active agent comprising a ribonucleic acid, a deoxyribonucleic acid or a protein is provided.

In particular embodiments, a conjugate comprising (1) a nanoparticle comprising an α-amino acid and a metal, and (2) a biologically active agent comprising small interfering ribonucleic acid (siRNA), micro ribonucleic acid (miRNA) or an aptamer/riboswitch, is provided.

In various embodiments, a conjugate comprising (1) a nanoparticle comprising an α-amino acid and cerium, and (2) a biologically active agent comprising small interfering ribonucleic acid (siRNA), micro ribonucleic acid (miRNA) or an aptamer/riboswitch, is provided.

In other various embodiments, a conjugate comprising (1) a nanoparticle comprising an α-amino acid and a cerium oxide, and (2) a biologically active agent comprising small interfering ribonucleic acid (siRNA), micro ribonucleic acid (miRNA) or an aptamer/riboswitch, is provided.

In particular embodiments, conjugates comprising deoxyribonucleic acid contain plasmid deoxyribonucleic acid.

In a particular embodiment of the invention, a conjugate comprising (1) a nanoparticle comprising an α-amino acid and a metal, and (2) a biologically active agent, is used as a cell transfection agent.

In a particular embodiment of the invention, a conjugate comprising (1) a nanoparticle comprising an α-amino acid and cerium, and (2) a biologically active agent, is used as a cell transfection agent.

In a particular embodiment of the invention, a conjugate comprising (1) a nanoparticle comprising an α-amino acid and a cerium oxide, and (2) a biologically active agent, is used as a cell transfection agent.

In various embodiments of the invention, a conjugate comprising (1) a nanoparticle comprising an α-amino acid, optionally cerium or a cerium oxide, and (2) a biologically active agent, are used as a stem-cell promoting factor, a cell reprogramming factor, a radioprotective factor, a vaccine or a drug delivery vehicle.

In a particular embodiment of the invention, a process of transfecting a cell, comprising: contacting a cell with a conjugate comprising 1) a nanoparticle comprising an α-amino acid, optionally cerium or a cerium oxide, and 2) a biologically active agent; is provided. In a particular embodiment, a process of transfecting a cell, comprising:
contacting a cell with a conjugate comprising 1) a nanoparticle comprising an α-amino acid, optionally cerium or a cerium oxide, and 2) a biologically active agent; is provided, wherein said cell is part of a tissue or cell culture in an in vitro setting.

In a particular embodiment, a process of transfecting a cell, comprising:
contacting a cell with a conjugate comprising 1) a nanoparticle comprising an α-amino acid, optionally cerium or a cerium oxide, and 2) a biologically active agent; is provided, wherein said cell is part of a living organism.

In various embodiments, a process of transfecting a cell, comprising:
contacting a cell with a conjugate comprising 1) a nanoparticle comprising an α-amino acid, optionally cerium or a cerium oxide, and 2) a biologically active agent; is provided, wherein said biologically active agent is comprised of ribonucleic acid, deoxyribonucleic acid or protein.

In particular embodiments, a process of transfecting a cell, comprising:
contacting a cell with a conjugate comprising 1) a nanoparticle comprising an α-amino acid, optionally cerium or a cerium oxide, and 2) a ribonucleic acid; is provided, wherein said ribonucleic acid is small interfering ribonucleic acid, micro ribonucleic acid or an aptamer/riboswitch.

In particular embodiments, a process of transfecting a cell, comprising:
contacting a cell with a conjugate comprising 1) a nanoparticle comprising an α-amino acid, optionally cerium or a cerium oxide, and 2) a biologically active agent; is provided, wherein said conjugate is used as a stem-cell promoting factor or a cell reprogramming factor.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent.

Quantitative assessments of the particle size of the nanoparticle dispersions were made by a number of techniques.

Dynamic light scattering (DLS) measurements were obtained using a Brookhaven 90Plus
Particle Size Analyzer (Brookhaven Instruments Corp., Holtzville, N.Y., U.S.A.) equipped with a quartz cuvette. Reported DLS sizes are the lognormal number weighted parameter. DLS sizes are typically larger than sizes yielded by other techniques because the DLS includes contributions from adsorbed ions or molecules that constitute the solvation sphere of the particle.

Particle size estimation by peak-width analysis of X-ray diffraction (XRD) spectra was done using the Scherrer method. Sample preparation for the XRD measurements was done as follows: liquid samples were mixed lightly, placed in a Telfon boat, allowed to dry under a heat lamp for several hours (until nearly dry), the resulting concentrated liquid was then placed onto a zero background quartz disk, allowed to dry under the heat lamp, and then dried in an oven at either room temperature or at about 80° C. for four hours under a dry nitrogen atmosphere. The coated disk was then analyzed by XRD using a nitrogen gas dry cell attachment. The XRD spectra were recorded on a Rigaku D2000 diffractometer equipped with copper rotating anode, diffraction beam graphite monochrometer tuned to copper K-alpha radiation, and a scintillation detector. Alternatively, the size of the nanoparticles could be determined by direct analysis of transmission electron microscopy (TEM) images of the particles.

Nanoparticle Charge Assessment

A quantitative assessment of the nanoparticle charge was made by measuring the zeta potential of the nanoparticle dispersions using a Zetasizer Nano ZS from Malvern Instruments (Malvern, Worcestershire, UK).

Preparation of Nanoparticles with Cerium and Arginine

Example 1a

WC-Bio-9a: 0.1 DL-Arginine/Cerium

Into a 600 ml glass beaker containing a magnetic stir bar was introduced 500 ml of high purity (HP) water. A 0.415 gm quantity of DL-arginine was dissolved in this volume, forming an alkaline solution. A 10.0 gm quantity of $Ce(NO_3)_3 \cdot 6(H_2O)$ was added, dissolved with stirring, resulting in a solution pH of about pH 6. The molar ratio of DL-arginine to cerium ion was 0.1. Base in the form of ammonium hydroxide was added. Then a 10 ml solution containing 1.20 gm of 50% $H_2O_2$ (0.75 molar ratio of $H_2O_2$ to cerium ion) was added slowly to the cerium and arginine solution mixture. The reaction product was then heated to 40° C. for 1 hour. After cooling, the final product dispersion displayed a high degree of Tyndall scattering when illuminated with a low intensity LASER beam, indicating it contained well-dispersed colloidal particles. Particle size analysis by dynamic light scattering indicated a hydrodynamic diameter of 93.1 nm with a polydispersity of 0.111.

Example 1b

WC-Bio-10a: 0.4 DL-Arginine/Cerium

Into a 600 ml glass beaker with a magnetic stir bar was introduced 500 ml of high purity (HP) water. A 1.605 gm quantity of DL-arginine was dissolved in this volume and the solution was heated to about 40° C., thereby forming an alkaline solution. An aqueous solution containing a 10.0 gm quantity of $Ce(NO_3)_3 \cdot 6(H_2O)$ was added under high shear mixing conditions provided by a Silverson L4RT high shear mixer operated at about 5000 RPM, resulting in a pale orange colored solution of about pH 7.9. The molar ratio of DL-arginine to cerium ion was 0.4. Then a 10 ml solution containing 1.2 gm of 50% $H_2O_2$ (0.75 molar ratio of $H_2O_2$ to cerium ion) was added slowly to the cerium and arginine solution mixture, which lowered the pH to about 3.4, and formed a turbid dark brown/orange suspension. The pH was further adjusted to about 2 by the addition of 1N $HNO_3$, thereby forming a clear orange liquid. The reaction product was then stirred with a magnetic stir bar for 1 hour at 40° C. After cooling overnight, the reaction product was washed to remove salts by diafiltration, during which about two turnover volumes of HP water were added, and then concentrated to a final volume of about 150 ml, an ionic conductivity of about 1.6 mS/cm and a pH of about 3.3.

The final product dispersion was a clear yellow/orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.6 nm with a polydispersity of 0.296, and a zeta potential of 39.4 mV.

The procedures of Example 1b were repeated and yielded similar results. Specifically, a clear yellow/orange liquid with an ionic conductivity of 2.52 mS/cm and a final pH of about 3.06, displayed a high degree of Tyndall scattering when illuminated with a low intensity LASER beam, a hydrodynamic diameter of 6.8 nm with a polydispersity of 0.265, and a zeta potential of 31.0 mV.

Example 1c

WC-Bio-9b: 0.5 DL-Arginine/Cerium

Into a 600 ml glass beaker containing a magnetic stir bar was introduced 500 ml of high purity (HP) water. A 2.006 gm quantity of DL-arginine was dissolved in this volume and the solution was heated to about 40° C., forming an alkaline solution. A 10.0 gm quantity of $Ce(NO_3)_3 \cdot 6(H_2O)$ was added, dissolved with stirring, resulting in a solution pH of about pH 6. The molar ratio of DL-arginine to cerium ion was 0.5. Then a 10 ml solution containing 1.20 gm of 50% $H_2O_2$ (0.75 molar ratio of $H_2O_2$ to cerium ion) was added slowly to the cerium and arginine solution mixture, which lowered the pH to about 4, and formed a turbid white suspension. The pH was further adjusted to about 3 by the addition of 1N $HNO_3$, thereby forming a clear suspension. The reaction product was then held at 40° C. for 1 hour. After cooling, the final product dispersion was a clear liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.7 nm with a polydispersity of 0.27.

Example 1d

WC-Bio-10b: 0.8 DL-Arginine/Cerium

Into a 600 ml glass beaker containing a magnetic stir bar was introduced 500 ml of high purity (HP) water. A 3.21 gm quantity of DL-arginine was dissolved in this volume and the solution was heated to about 40° C., forming an alkaline solution. A 10.0 gm quantity of $Ce(NO_3)_3 \cdot 6(H_2O)$ was added under high shear mixing conditions provided by a Silverson L4RT high shear mixer operated at about 5000 RPM, resulting in a solution of about pH 8. The molar ratio of DL-arginine to cerium ion was 0.8. Then a 10 ml solution containing 1.20 gm of 50% $H_2O_2$ (0.75 molar ratio of $H_2O_2$ to cerium ion) was added slowly to the cerium and arginine solution mixture, which lowered the pH to about 3.4. The pH was further adjusted to about 2 by the addition of 1N $HNO_3$. The reaction product was then held at 40° C. for 1 hour. After cooling, a portion of the product suspension was then washed to remove salts by diafiltration, during which about two turnover volumes of HP water were added, and then concentrated to a final ionic conductivity of about 2 mS/cm and a pH of 3.1.

The final product dispersion was a clear yellow liquid that displayed a high degree of Tyndall scattering when illuminated with a low intensity LASER beam, indicating it contained well-dispersed colloidal particles.

Analysis of the XRD spectra shown in FIG. 1 indicated the presence of a major crystalline phase iso-structural with $CeO_2$ (PDF #34-394, cerianite) for the nanoparticles prepared in Example 1d. An average crystallite size of 2.8 nm was determined in the $CeO_2$ (220) direction for these nanoparticles using the Scherrer technique.

Particle size analysis by dynamic light scattering indicated a hydrodynamic diameter of 11.5 nm with a polydispersity of 0.333. The substantially larger particle size determined by DLS relative to that determined by XRD, suggests, perhaps, the presence of a substantial solvation sphere around the nanoparticles, and/or some small amount of agglomerated nanoparticles.

Zeta potential measurements showed a charge of +38.5 mV for these nanoparticles.

Example 1e

WC-Bio-10:1.0 DL-Arginine/Cerium

Into a 600 ml glass beaker containing a magnetic stir bar was introduced 500 ml of high purity (HP) water. A 4.01 gm quantity of DL-arginine was dissolved in this volume and the solution was heated to about 40° C., forming an alkaline solution. A 10.0 gm quantity of $Ce(NO_3)_3 \cdot 6(H_2O)$ was added under high shear mixing conditions provided by a Silverson L4RT high shear mixer operated at about 5000 RPM, resulting in a solution pH of about pH 6. The molar ratio of DL-arginine to cerium ion was 1.0. Then a 10 ml solution containing 1.20 gm of 50% $H_2O_2$ (0.75 molar ratio of $H_2O_2$ to cerium ion) was added slowly to the cerium and arginine solution mixture, which lowered the pH to about 4, and formed a turbid dark brown/orange suspension. The pH was further adjusted to about 2.1 by the addition of 1N $HNO_3$, thereby forming a clear brown suspension. The product suspension was then washed to remove salts by diafiltration, during which about two turnover volumes of HP water were added, and then concentrated to a final ionic conductivity of about 2.1 mS/cm and a pH of 2.8.

The final product dispersion was a clear yellow/orange liquid that displayed a high degree of Tyndall scattering when illuminated with a low intensity LASER beam, indicating it contained well-dispersed colloidal particles. FIG. 2 is a TEM image representative of the particles prepared in Example 1e, wherein individual (non-agglomerated) particles in the range of about 2-3 nm in diameter are clearly shown.

Particle size analysis by dynamic light scattering indicated a hydrodynamic diameter of 7.85 nm with a polydispersity of 0.202.

The above procedures were repeated twice, yielding substantially similar results. More specifically, DLS particle sizes of 7.20 nm with a polydispersity of 0.145, and 5.70 nm with a polydispersity of 0.190, were obtained from replicate preparations.

Example 1f

WC-Bio-10c: 1.2 DL-Arginine/Cerium

Into a 600 ml glass beaker containing a magnetic stir bar was introduced 500 ml of high purity (HP) water. A 4.82 gm quantity of DL-arginine was dissolved in this volume and the solution was heated to about 40° C., forming an alkaline solution. A 10.0 gm quantity of $Ce(NO_3)_3 \cdot 6(H_2O)$ was added, dissolved with stirring, resulting in a solution pH of about pH 6. The molar ratio of DL-arginine to cerium ion was 1.2. Then a 10 ml solution containing 1.20 gm of 50% $H_2O_2$ (0.75 molar ratio of $H_2O_2$ to cerium ion) was added slowly to the cerium and arginine solution mixture, which lowered the pH to about 4, and formed a turbid dark brown/orange suspension. The pH was further adjusted to about 2 by the addition of 1N $HNO_3$, thereby forming a clear brown suspension. The product suspension was then washed to remove salts by diafiltration, during which about two turnover volumes of HP water were added, and then concentrated to a final ionic conductivity of about 1.9 mS/cm and a pH of 2.9.

The final product dispersion was a clear yellow/orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.85 nm with a polydispersity of 0.232. Zeta potential measurements showed a charge of +37.7 mV for these nanoparticles.

Example 1g

WC-Bio-10d: 1.6 DL-Arginine/Cerium

Into a 600 ml glass beaker containing a magnetic stir bar was introduced 500 ml of high purity (HP) water. A 6.42 gm quantity of DL-arginine was dissolved in this volume and the solution was heated to about 40° C., forming an alkaline solution. A 10.0 gm quantity of $Ce(NO_3)_3 \cdot 6(H_2O)$ was added, dissolved with stirring, resulting in a solution pH of about pH 6. The molar ratio of DL-arginine to cerium ion was 1.6. Then a 10 ml solution containing 1.20 gm of 50% $H_2O_2$ (0.75 molar ratio of $H_2O_2$ to cerium ion) was added slowly to the cerium and arginine solution mixture, which lowered the pH to about 4, and formed a turbid dark brown/orange suspension. The pH was further adjusted to about 2 by the addition of 1N $HNO_3$, thereby forming a clear brown suspension. The product suspension was then washed to remove salts by diafiltration, during which about two turnover volumes of HP water were added, and then concentrated to a final ionic conductivity of about 2.3 mS/cm and a pH of 2.5.

The final product dispersion was a clear yellow/orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 6.95 nm with a polydispersity of 0.291.

Preparation of Nanoparticles with Cerium and Histidine

Example 2a

WC-Bio-15a: 0.2 L-Histidine/Cerium

Into a 600 ml glass beaker containing a magnetic stir bar was introduced 500 ml of high purity (HP) water. A 0.715 gm quantity of L-histidine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-histidine to cerium ion was 0.2. Then a 10 ml solution containing 1.20 gm of 50% $H_2O_2$ (0.75 molar ratio of $H_2O_2$ to cerium ion) was added slowly to the cerium and histidine solution mixture. The pH was further adjusted to about 2.1 by the addition of 1N $HNO_3$, thereby forming a clear brown suspension. The product suspension was then washed to remove salts by diafiltration, during which about two turnover volumes of HP water were added, and then concentrated to a final ionic conductivity of about 2.1 mS/cm and a pH of 3.1.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 13.35 nm with a polydispersity of 0.30.

Zeta potential measurements showed a charge of +38.5 mV for these nanoparticles.

Example 2b

WC-Bio-15b: 0.4 L-Histidine/Cerium

Into a 600 ml glass beaker containing a magnetic stir bar was introduced 500 ml of high purity (HP) water. A 1.429 gm quantity of L-histidine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-histidine to cerium ion was 0.4. Then a 10 ml solution containing 1.20 gm of 50% $H_2O_2$ (0.75 molar ratio of $H_2O_2$ to cerium ion) was added slowly to the cerium and histidine solution mixture. The pH was further adjusted to about 2.1 by the addition of 1N $HNO_3$, thereby forming a clear brown suspension. The product suspension was then washed to remove salts by diafiltration, during which about two turnover volumes of HP water were added, and then concentrated to a final ionic conductivity of about 2.1 mS/cm and a pH of 3.2.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 17.25 nm with a polydispersity of 0.267. Analysis of the XRD spectrum shown as spectrum (a) of FIG. 3 indicated the presence of a major crystalline phase iso-structural with $CeO_2$ (PDF #34-394, cerianite) for the nanoparticles prepared in Example 2b. Spectrum (a) of FIG. 3 also contains a peak at 19 degree two-theta, indicative of the presence of an additional crystalline phase. After annealing of the mounted X-ray sample of Example 2b in a Deltech furnace set at 200° C. for 30 minutes, the 19 degree two-theta peak was removed and the $CeO_2$ assigned peaks became more intense, but with similar peak width, indicating little or no change in crystallite size upon annealing. An average crystallite size of 3.6 nm was determined in the $CeO_2$ (220) direction for the annealed nanoparticles using the Scherrer technique.

Zeta potential measurements showed a charge of +40.4 mV for these nanoparticles.

Example 2c

WC-Bio-15c: 0.8 Histidine/Cerium

Into a 600 ml glass beaker containing a magnetic stir bar was introduced 500 ml of high purity (HP) water. A 2.858 gm quantity of L-histidine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-histidine to cerium ion was 0.8. Then a 10 ml solution containing 1.20 gm of 50% $H_2O_2$ (0.75 molar ratio of $H_2O_2$ to cerium ion) was added slowly to the cerium and histidine solution mixture. The pH was further adjusted to about 2.1 by the addition of 1N $HNO_3$, thereby forming a clear brown suspension. The product suspension was then washed to remove salts by diafiltration, during which about two turnover volumes of HP water were added, and then concentrated to a final ionic conductivity of about 2.0 mS/cm and a pH of 3.1.

The product dispersion was a clear orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 6.8 nm with a polydispersity of 0.278.

Example 2d

WC-Bio-15d: 1.0 Histidine/Cerium

Into a 600 ml glass beaker containing a magnetic stir bar was introduced 500 ml of high purity (HP) water. A 3.57 gm quantity of L-histidine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-histidine to cerium ion was 1.0. Then a 10 ml solution containing 1.20 gm of 50% $H_2O_2$ (0.75 molar ratio of $H_2O_2$ to cerium ion) was added slowly to the cerium and histidine solution mixture. The pH was further adjusted to about 2.1 by the addition of 1N $HNO_3$, thereby forming a clear brown suspension. The product suspension was then washed to remove salts by diafiltration, during which about two turnover volumes of HP water were added, and then concentrated to a final ionic conductivity of about 1.9 mS/cm and a pH of 2.9.

The product dispersion was a clear orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 9.7 nm with a polydispersity of 0.297.

Example 2e

WC-Bio-15e: 1.2 L-Histidine/Cerium

Into a 600 ml glass beaker containing a magnetic stir bar was introduced 500 ml of high purity (HP) water. A 4.287 gm quantity of L-histidine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-histidine to cerium ion was 1.2. Then a 10 ml solution containing 1.20 gm of 50% $H_2O_2$ (0.75 molar ratio of $H_2O_2$ to cerium ion) was added slowly to the cerium and histidine solution mixture. The pH was further adjusted to about 3 by the addition of 1N $HNO_3$, thereby forming a clear suspension. The reaction product was then heated to 40° C. for 1 hour. After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 9.3 nm with a polydispersity of 0.327.

A sample portion was prepared for powder X-ray diffraction analysis by placement in a Teflon boat, drying under a heat lamp for several hours (until nearly dried), the resulting concentrated liquid was then placed onto a zero background quartz disk, allowed to dry under the heat lamp, and then dried in an oven for four hours at room temperature under a dry nitrogen atmosphere. Each coated disk was then analyzed by XRD in a $N_2$ dry cell attachment. Evidence of crystallinity is shown by the diffraction peaks in FIG. 4. More specifically, the nanoparticles formed in this example are characterized by powder XRD peak positions ranging from 7-10 degrees Two-Theta, from 13-16 degrees Two-Theta, from 17-19 degrees Two-Theta, from 22-24 degrees Two-Theta, from 26-29 degrees Two-Theta, from 30-32 degrees Two-Theta, from 34-36 degrees Two-Theta, from 39-41 degrees Two-Theta, from 42-43 degrees Two-Theta, from 45-47 degrees Two-Theta, from 48-50 degrees Two-Theta, from 53-54 degrees Two-Theta or from 55-57 degrees Two-Theta. While it is possible to assign crystalline $CeO_2$ a possible minority phase, the majority of the crystalline product of this example is a phase with a substantially larger unit cell than $CeO_2$.

Zeta potential measurements showed a charge of +44.9 mV for these nanoparticles.

Preparation of Nanoparticles with Cerium and Arginine/Histidine

Example 3a

WC-Bio-10i: 0.4 (0.3 DL-Arginine/0.7 L-Histidine)/Cerium

Into a 600 ml glass beaker containing a magnetic stir bar was introduced 500 ml of high purity (HP) water. A 0.481 gm quantity of DL-arginine and a 0.999 gm quantity of DL-histidine (molar ratio of DL-arginine to L-histidine of 0.3/0.7) were dissolved in this volume and the solution mixture was heated to about 40° C. A 10.0 gm quantity of $Ce(NO_3)_3 \cdot 6(H_2O)$ was added, thereby forming a molar ratio of total amino acids to cerium ion of 0.4. Then a 10 ml solution containing 1.20 gm of 50% $H_2O_2$ (0.75 molar ratio of $H_2O_2$ to cerium ion) was added slowly to the cerium and arginine/histidine solution mixture. The pH was further adjusted to about 2.1 by the addition of 1N $HNO_3$, thereby forming a clear suspension. The reaction product was then heated to 40° C. for 1 hour. The product suspension was then washed to remove salts by diafiltration, during which about two turnover volumes of HP water were added, and then concentrated to a final ionic conductivity of about 2.54 mS/cm and a pH of 3.05.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 8.0 nm with a polydispersity of 0.32. Zeta potential measurements showed a charge of +31.2 mV for these nanoparticles.

Examples 3b-3k (DL-Arginine/L-Histidine)/Cerium

The procedures of Example 3a were repeated except that the molar ratio of DL-arginine to L-histidine and the molar ratio of total amino acids to cerium ion (AA:Ce) were varied as shown in Table 1 below:

TABLE 1

| Ex. | Molar Ratio of Amino Acid Stabilizers | AA:Ce | DLS (nm) | Zeta (mV) |
|---|---|---|---|---|
| 3a | DL-Arginine (0.3) L-Histidine (0.7) | 0.4:1 | 8.0 | 31.2 |
| 3b | DL-Arginine (0.9) L-Histidine (0.1) | 0.5:1 | 7.9 | — |
| 3c | DL-Arginine (0.7) L-Histidine (0.3) | 0.5:1 | 6.8 | — |
| 3d | DL-Arginine (0.5) L-Histidine (0.5) | 0.5:1 | 8.0 | — |
| 3e | DL-Arginine (0.77) L-Histidine (0.23) | 0.52:1 | 6.9 | 30.3 |
| 3f | DL-Arginine (0.6) L-Histidine (0.4) | 0.68:1 | 12.8 | 26.9 |
| 3g | DL-Arginine (0.8) L-Histidine (0.2) | 0.7:1 | 7.2 | — |
| 3h | DL-Arginine (0.7) L-Histidine (0.3) | 0.75:1 | 6.8 | — |
| 3i | DL-Arginine (0.9) L-Histidine (0.1) | 1.0:1 | 7.1 | 42 |
| 3j | DL-Arginine (0.7) L-Histidine (0.3) | 1.0:1 | 7.1 | 29 |
| 3k | DL-Arginine (0.5) L-Histidine (0.5) | 1.0:1 | 8.3 | 46 |

The product dispersions were clear yellow liquids that displayed a high degree of Tyndall scattering when illuminated with a low intensity LASER beam, indicating that they contained well-dispersed colloidal particles. Particle size analysis by dynamic light scattering indicated hydrodynamic diameters of about 7-12 nm.

Zeta potential measurements for those dispersions of Example 3 that were examined examined showed a positive charge in the range of about 20-50 mV. We emphasize that a step of adjusting the reaction mixture to a pH less than about 3 was included in the process for preparing the nanoparticle dispersions in Examples 3a-3k. In contrast, if such an inventive step is omitted, or if a substantial amount of a base such as ammonium hydroxide is added to the reaction mixture, then nanoparticle dispersion with negative zeta potentials in the range of about −15 mV to about −30 mV are generally produced.

Electron diffraction spectra were obtained for the nanoparticle dispersions prepared in Examples 3i, 3j and 3k as shown in FIGS. 5, 7 and 8, respectively. In each spectrum, diffraction rings characteristic only of cerium dioxide were observed.

Preparation of Nanoparticles with Cerium and Lysine

Example 4a

WC-Bio-13a: 0.4 L-Lysine/Cerium

Into a 600 ml glass beaker containing a magnetic stir bar was introduced 500 ml of high purity (HP) water. A 1.347 gm quantity of L-lysine was dissolved in this volume and the solution was heated to about 40° C., forming an alkaline solution. A 10.0 gm quantity of $Ce(NO_3)_3 \cdot 6(H_2O)$ was added, about pH 6. The molar ratio of L-lysine to cerium ion was 0.4. Then a 10 ml solution containing 1.20 gm of 50% $H_2O_2$ (0.75 molar ratio of $H_2O_2$ to cerium ion) was added slowly to the cerium and lysine solution mixture. The pH was further adjusted to about 3 by the addition of 1N $HNO_3$, thereby forming a clear suspension. The reaction product was then heated to 40° C. for 1 hour. After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.25 nm with a polydispersity of 0.278.

Zeta potential measurements showed a charge of +37.3 mV for these nanoparticles.

Example 4b

WC-Bio-13b: 0.8 L-Lysine/Cerium

Into a 600 ml glass beaker containing a magnetic stir bar was introduced 500 ml of high purity (HP) water. A 2.693 gm quantity of L-lysine was dissolved in this volume and the solution was heated to about 40° C., forming an alkaline solution. A 10.0 gm quantity of Ce(NO$_3$)$_3$·6(H$_2$O) was added, about pH 6. The molar ratio of L-lysine to cerium ion was 0.8. Then a 10 ml solution containing 1.20 gm of 50% H$_2$O$_2$ (0.75 molar ratio of H$_2$O$_2$ to cerium ion) was added slowly to the cerium and lysine solution mixture. The pH was further adjusted to about 3 by the addition of 1N HNO$_3$, thereby forming a clear suspension. The reaction product was then heated to 40° C. for 1 hour. After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.95 nm with a polydispersity of 0.297.

Zeta potential measurements showed a charge of +41.1 mV for these nanoparticles.

Example 4c

WC-Bio-13c: 1.2 L-Lysine/Ceriunn

Into a 600 ml glass beaker containing a magnetic stir bar was introduced 500 ml of high purity (HP) water. A 4.040 gm quantity of L-lysine was dissolved in this volume and the solution was heated to about 40° C., forming an alkaline solution. A 10.0 gm quantity of Ce(NO$_3$)$_3$·6(H$_2$O) was added, about pH 6. The molar ratio of L-lysine to cerium ion was 1.2. Then a 10 ml solution containing 1.20 gm of 50% H$_2$O$_2$ (0.75 molar ratio of H$_2$O$_2$ to cerium ion) was added slowly to the cerium and lysine solution mixture. The pH was further adjusted to about 2.45 by the addition of 1N HNO$_3$, thereby forming a clear suspension. The reaction product was then heated to 40° C. for 1 hour. After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.95 nm with a polydispersity of 0.297.

A sample portion was prepared for powder X-ray diffraction analysis by placement in a Teflon boat, drying under a heat lamp for several hours (until nearly dried), the resulting concentrated liquid was then placed onto a zero background quartz disk, allowed to dry under the heat lamp, and then dried in an oven for four hours at room temperature under a dry nitrogen atmosphere. Each coated disk was then analyzed by XRD in a N$_2$ dry cell attachment. Evidence of crystallinity is shown by the diffraction peaks in FIG. 4. More specifically, the nanoparticles formed in this example are characterized by powder XRD peak positions ranging from 7-10 degrees Two-Theta, from 13-16 degrees Two-Theta, from 17-19 degrees Two-Theta, from 22-24 degrees Two-Theta, from 26-29 degrees Two-Theta, from 30-32 degrees Two-Theta, from 34-36 degrees Two-Theta, from 39-41 degrees Two-Theta, from 42-43 degrees Two-Theta, from 45-47 degrees Two-Theta, from 48-50 degrees Two-Theta, from 53-54 degrees Two-Theta or from 55-57 degrees Two-Theta. While it is possible to assign crystalline CeO$_2$ a possible minority phase, the majority of the crystalline product of this example is a phase with a substantially larger unit cell than CeO$_2$.

Zeta potential measurements showed a charge of +37.7 mV for these nanoparticles.

Preparation of Nanoparticles with Cerium and Serine

Example 5a

WC-Bio-11: 0.8 DL-Serine/Cerium

Into a 600 ml glass beaker containing a magnetic stir bar was introduced 500 ml of high purity (HP) water. A 1.936 gm quantity of DL-serine was dissolved in this volume and the solution was heated to about 40° C. A 10.0 gm quantity of Ce(NO$_3$)$_3$·6(H$_2$O) was added, thereby forming a molar ratio of L-serine to cerium ion of 0.8. Then a 10 ml solution containing 1.20 gm of 50% H$_2$O$_2$ (0.75 molar ratio of H$_2$O$_2$ to cerium ion) was added slowly to the cerium and serine solution mixture. The reaction product was then heated to 40° C. for 1 hour, after which the solution pH was about 3.8. The product suspension was then washed to remove salts by diafiltration, during which about two turnover volumes of HP water were added, and then concentrated to a final ionic conductivity of about 2.3 mS/cm and a pH of 3.1.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 35.2 nm with a polydispersity of 0.152.

Preparation of Nanoparticles with Cerium and Arginine/Serine

Example 6a

WC-Bio-11h: 0.4 (0.7 DL-Arginine/0.3 DL-Serine)/Cerium

Into a 600 ml glass beaker containing a magnetic stir bar was introduced 500 ml of high purity (HP) water. A 1.124 gm quantity of DL-arginine and a 0.29 gm quantity of DL-serine (molar ratio of DL-arginine to DL-serine of 0.7/0.3) were dissolved in this volume and the solution mixture was heated to about 40° C. A 10.0 gm quantity of Ce(NO$_3$)$_3$·6(H$_2$O) was added, thereby forming a molar ratio of total amino acids to cerium ion of 0.4. Then a 10 ml solution containing 1.20 gm of 50% H$_2$O$_2$ (0.75 molar ratio of H$_2$O$_2$ to cerium ion) was added slowly to the cerium and arginine/serine solution mixture. The pH was further adjusted to about 2.1 by the addition of 1N HNO$_3$, thereby forming a clear suspension. The reaction product was then heated to 40° C. for 1 hour. The product suspension was then washed to remove salts by diafiltration, during which about two turnover volumes of HP water were added, and then concentrated to a final ionic conductivity of about 2.45 mS/cm and a pH of 3.2.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 6.5 nm with a polydispersity of 0.278. Zeta potential measurements showed a charge of +37.4 mV for these nanoparticles.

Example 6b

WC-Bio-11i: 0.4 (0.3 DL-Arginine/0.7 DL-Serine)/Cerium

Into a 600 ml glass beaker containing a magnetic stir bar was introduced 500 ml of high purity (HP) water. A 0.482 gm quantity of DL-arginine and a 0.677 gm quantity of DL-serine (molar ratio of DL-arginine to DL-serine of 0.3/0.7) were dissolved in this volume and the solution mixture was heated to about 40° C. A 10.0 gm quantity of Ce(NO$_3$)$_3$·6(H$_2$O) was added, thereby forming a molar ratio of total amino acids to cerium ion of 0.4. Then a 10 ml solution containing 1.20 gm of 50% H$_2$O$_2$ (0.75 molar ratio of H$_2$O$_2$ to cerium ion) was added slowly to the cerium and arginine/serine solution mixture. The pH was further adjusted to about 2.1 by the addition of 1N $HNO_3$, thereby forming a clear suspension. The reaction product was then heated to 40° C. for 1 hour. The product suspension was then washed to remove salts by diafiltration, during which about two turnover volumes of HP water were added, and then concentrated to a final ionic conductivity of about 2.2 mS/cm and a pH of 3.0.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 13.7 nm with a polydispersity of 0.330.

Example 6c

WC-Bio-11f: 0.52 (0.77 DL-Arginine/0.23 DL-Serine)/Cerium

Into a 600 ml glass beaker containing a magnetic stir bar was introduced 500 ml of high purity (HP) water. A 1.607 gm quantity of DL-arginine and a 0.289 gm quantity of DL-serine (molar ratio of DL-arginine to DL-serine of 0.77/0.23) were dissolved in this volume and the solution mixture was heated to about 40° C. A 10.0 gm quantity of $Ce(NO_3)_3 \cdot 6(H_2O)$ was added, thereby forming a molar ratio of total amino acids to cerium ion of 0.52. Then a 10 ml solution containing 1.20 gm of 50% $H_2O_2$ (0.75 molar ratio of $H_2O_2$ to cerium ion) was added slowly to the cerium and arginine/serine solution mixture. The pH was further adjusted to about 2.1 by the addition of 1N $HNO_3$, thereby forming a clear suspension. The reaction product was then heated to 40° C. for 1 hour. The product suspension was then washed to remove salts by diafiltration, during which about two turnover volumes of HP water were added, and then concentrated to a final ionic conductivity of about 2.3 mS/cm and a pH of 3.0.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.55 nm with a polydispersity of 0.284.

Example 6d

WC-Bio-11g: 0.68 (0.59 DL-Arginine/0.41 DL-Serine)/Cerium

Into a 600 ml glass beaker containing a magnetic stir bar was introduced 500 ml of high purity (HP) water. A 1.611 gm quantity of DL-arginine and a 0.674 gm quantity of DL-serine (molar ratio of DL-arginine to DL-serine of 0.59/0.41) were dissolved in this volume and the solution mixture was heated to about 40° C. A 10.0 gm quantity of $Ce(NO_3)_3 \cdot 6(H_2O)$ was added, thereby forming a molar ratio of total amino acids to cerium ion of 0.68. Then a 10 ml solution containing 1.20 gm of 50% $H_2O_2$ (0.75 molar ratio of $H_2O_2$ to cerium ion) was added slowly to the cerium and arginine/serine solution mixture. The pH was further adjusted to about 2.1 by the addition of 1N $HNO_3$, thereby forming a clear suspension. The reaction product was then heated to 40° C. for 1 hour.

The product suspension was then washed to remove salts by diafiltration, during which about two turnover volumes of HP water were added, and then concentrated to a final ionic conductivity of about 2.3 mS/cm and a pH of 2.8.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 9.20 nm with a polydispersity of 0.270. Zeta potential measurements showed a charge of +40.8 mV for these nanoparticles.

Preparation of Nanoparticles with Cerium and Threonine

Example 7a

WC-Bio-12: 0.8 DL-Threonine/Cerium

Into a 600 ml glass beaker containing a magnetic stir bar was introduced 500 ml of high purity (HP) water. A 2.194 gm quantity of DL-threonine was dissolved in this volume. A 10.0 gm quantity of $Ce(NO_3)_3 \cdot 6(H_2O)$ was added, thereby forming a molar ratio of L-threonine to cerium ion of 0.8. Then a 10 ml solution containing 2.40 gm of 50% $H_2O_2$ (1.5 molar ratio of $H_2O_2$ to cerium ion) was added slowly to the cerium and threonine solution mixture. The pH was further adjusted to about 4.3. The reaction product was then heated to 40° C. for 1 hour. The product suspension was then washed to remove salts by diafiltration, during which about two turnover volumes of HP water were added, and then concentrated to a final ionic conductivity of about 3.05 mS/cm and a pH of 3.1.

After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 29.6 nm with a polydispersity of 0.328.

Example 7b

WC-Bio-12a: 1.0 DL-Threonine/Cerium

Into a 600 ml glass beaker containing a magnetic stir bar was introduced 500 ml of high purity (HP) water. A 2.743 gm quantity of DL-threonine was dissolved in this volume. A 5.0 gm quantity of $Ce(NO_3)_3 \cdot 6(H_2O)$ was added, thereby forming an equimolar ratio of L-threonine to cerium ion. Then a 10 ml solution containing 2.40 gm of 50% $H_2O_2$ (3.0 molar ratio of $H_2O_2$ to cerium ion) was added slowly to the cerium and threonine solution mixture. The pH was further adjusted to about 3.5. The reaction product was then heated to 80° C. for 1 hour.

After cooling, the product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 17.6 nm with a polydispersity of 0.665.

Example 7c

WC-Bio-12b: 1.6 DL-Threonine/Cerium

The procedures of Example 7b were repeated, except that the amount of threonine was increased to 4.389 gm (1.6 molar ratio of threonine to cerium ion), and the solution mixture and reaction product were not heated. The product suspension was then washed to remove salts by diafiltration, during which about two turnover volumes of HP water were added, and then concentrated to a final ionic conductivity of about 2.7 mS/cm and a pH of 3.0.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 41.4 nm with a polydispersity of 0.211.

Preparation of Nanoparticles with Cerium and Alanine

Example 8a

WC-Bio-7c: 0.8 L-Alanine/Cerium

Into a 600 ml glass beaker containing a magnetic stir bar was introduced 500 ml of high purity (HP) water. A 1.64 gm quantity of L-alanine was dissolved in this volume. A 10.0 gm quantity of $Ce(NO_3)_3 \cdot 6(H_2O)$ was added, thereby forming a molar ratio of L-alanine to cerium ion of 0.8. Then a 10 ml solution containing 1.20 gm of 50% $H_2O_2$ (0.75 molar ratio of $H_2O_2$ to cerium ion) was added slowly to the cerium and alanine solution mixture. The pH was further adjusted to about 2.8 by the addition of 1N $HNO_3$. The reaction product was then heated to 40° C. for 1 hour. The product suspension was then washed to remove salts by diafiltration, during which about two turnover volumes of HP water were added, and then concentrated to a final ionic conductivity of about 2.15 mS/cm and a pH of 3.3.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 31.0 nm with a polydispersity of 0.277.

Example 8b

WC-Bio-7a: 3.2 L-Alanine/Cerium

Into a 600 ml glass beaker containing a magnetic stir bar was introduced 500 ml of high purity (HP) water. A 6.566 gm quantity of L-alanine was dissolved in this volume. A 10.0 gm quantity of $Ce(NO_3)_3 \cdot 6(H_2O)$ was added, thereby forming a molar ratio of L-alanine to cerium ion of 3.2. Then a 10 ml solution containing 1.20 gm of 50% $H_2O_2$ (0.75 molar ratio of $H_2O_2$ to cerium ion) was added slowly to the cerium and alanine solution mixture. The pH was adjusted to about 4.0. The product suspension was then washed to remove salts by diafiltration, during which about two turnover volumes of HP water were added, and then concentrated to a final ionic conductivity of about 5.1 mS/cm and a pH of 3.2.

The product dispersion was a clear yellow liquid that displayed a high degree of Tyndall scattering when illuminated with a low intensity LASER beam, indicating it contained well-dispersed colloidal particles.

Analysis of the XRD spectra shown in FIG. 9 indicated the presence of a major crystalline phase iso-structural with $CeO_2$ (PDF #34-394, cerianite) for the nanoparticles prepared in Example 8b. An average crystallite size of 5.2 nm was determined in the $CeO_2$ (220) direction for these nanoparticles using the Scherrer technique.

Particle size analysis by dynamic light scattering indicated a hydrodynamic diameter of 34.3 nm with a polydispersity of 0.127. The substantially larger hydrodynamic diameter relative to the XRD crystallite size suggests that a substantial amount of nanoparticle agglomeration may be present in this particular example that used a larger ratio of amino acid to cerium ion.

Example 8c

WC-Bio-7a-2: 3.2 L-Alanine/Cerium

The procedures of Example 8b were repeated, except that the magnetic stir bar was replaced with a Silverson L4RT high shear mixer that was operated at about 5000 RPM. The product suspension was then washed to remove salts by diafiltration, during which about two turnover volumes of HP water were added, and then concentrated to a final ionic conductivity of about 5.1 mS/cm and a pH of 3.2.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 13.8 nm with a polydispersity of 0.265.

In comparison to the results of Example 8b, a substantial reduction in DLS particle size resulted from the use of more aggressive mixing conditions, demonstrating, perhaps, the importance of mixing on nanoparticle agglomeration.

Preparation of Nanoparticles with Cerium and Valine

Example 9

WC-Bio-20: 0.8 L-Valine/Cerium

Into a 600 ml glass beaker containing a magnetic stir bar was introduced 500 ml of high purity (HP) water. A 1.101 gm quantity of L-valine was dissolved in this volume. A 5.0 gm quantity of $Ce(NO_3)_3 \cdot 6(H_2O)$ was added, thereby forming a molar ratio of L-valine to cerium ion of 0.8. Then a 10 ml solution containing 1.2 gm of 50% $H_2O_2$ (1.5 molar ratio of $H_2O_2$ to cerium ion) was added slowly to the cerium and valine solution mixture. The pH was further adjusted to about 2.5 by the addition of 1N $HNO_3$. The reaction product was then heated to 40° C. for 1 hour. The product suspension was then washed to remove salts by diafiltration, during which about two turnover volumes of HP water were added, and then concentrated to a final ionic conductivity of about 2.37 mS/cm and a pH of 2.5.

The product dispersion was a clear tangerine colored liquid that displayed a high degree of Tyndall scattering when illuminated with a low intensity LASER beam, indicating it contained well-dispersed colloidal particles. Particle size analysis by dynamic light scattering indicated a hydrodynamic diameter of 17.3 nm with a polydispersity of 0.293.

Preparation of Nanoparticles with Cerium and Leucine

Example 10

WC-Bio-19: 0.8 L-Leucine/Cerium

Into a 600 ml glass beaker containing a magnetic stir bar was introduced 500 ml of high purity (HP) water. A 1.227 gm quantity of L-leucine was dissolved in this volume. A 5.0 gm quantity of $Ce(NO_3)_3 \cdot 6(H_2O)$ was added, thereby forming a molar ratio of L-leucine to cerium ion of 0.8. Then a 10 ml solution containing 1.2 gm of 50% $H_2O_2$ (1.5 molar ratio of $H_2O_2$ to cerium ion) was added slowly to the cerium and leucine solution mixture. The pH was further adjusted to about 2.1 by the addition of 1N $HNO_3$. The reaction product was then heated to 40° C. for 1 hour. The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 57.2 nm with a polydispersity of 0.179.

Preparation of Nanoparticles with Cerium and Isoleucine

Example 11

WC-Bio-18: 0.8 L-Isoleucine/Cerium

Into a 600 ml glass beaker containing a magnetic stir bar was introduced 500 ml of high purity (HP) water. A 1.233 gm quantity of L-Isoleucine was dissolved in this volume. A 5.0 gm quantity of $Ce(NO_3)_3 \cdot 6(H_2O)$ was added, thereby forming a molar ratio of L-Isoleucine to cerium ion of 0.8. Then a 10 ml solution containing 1.2 gm of 50% $H_2O_2$ (1.5 molar ratio of $H_2O_2$ to cerium ion) was added slowly to the cerium and isoleucine solution mixture. The pH was further adjusted to about 2.9 by the addition of 1N $HNO_3$. The reaction product was then heated to 40° C. for 1 hour. The product dispersion was a clear yellow liquid that displayed a high degree of Tyndall scattering when illuminated with a low intensity LASER beam, indicating it contained well-dispersed colloidal particles. Particle size analysis of the TEM image shown in FIG. 10 indicated a particle diameter distribution of about 2-5 nm.

Preparation of Nanoparticles with Cerium and Arginine/Isoleucine

Example 12a

WC-Bio-26: 0.4 (0.6 DL-Arginine/0.4 L-Isoleucine)/Cerium

Into a 600 ml glass beaker containing a magnetic stir bar was introduced 500 ml of high purity (HP) water. A 0.993 gm quantity of DL-Arginine and 0.493 gm quantity of L-Isoleucine were dissolved in this volume. A 10.0 gm quantity of $Ce(NO_3)_3 \cdot 6(H_2O)$ was added, thereby forming a molar ratio of amino acids to cerium ion of 0.4. Then a 10 ml solution containing 1.2 gm of 50% $H_2O_2$ (0.75 molar ratio of $H_2O_2$ to cerium ion) was added slowly to the cerium, arginine and isoleucine solution mixture. The pH was further adjusted to about 2.0 by the addition of 1N $HNO_3$. The reaction product was then heated to 40° C. for 1 hour.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 5.3 nm with a polydispersity of 0.259. Zeta potential measurements showed a charge of +34.2 mV for these nanoparticles.

Example 12b

WC-Bio-26a: 0.6 (0.6 DL-Arginine/0.4 L-Isoleucine)/Cerium

Into a 600 ml glass beaker containing a magnetic stir bar was introduced 500 ml of high purity (HP) water. A 1.489 gm quantity of DL-Arginine and 0.740 gm quantity of L-Isoleucine were dissolved in this volume. A 10.0 gm quantity of $Ce(NO_3)_3 \cdot 6(H_2O)$ was added, thereby forming a molar ratio of amino acids to cerium ion of 0.6. Then a 10 ml solution containing 1.2 gm of 50% $H_2O_2$ (0.75 molar ratio of $H_2O_2$ to cerium ion) was added slowly to the cerium, arginine and isoleucine solution mixture. The pH was further adjusted to about 2.0 by the addition of 1N $HNO_3$. The reaction product was then heated to 40° C. for 1 hour.

The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 8.05 nm with a polydispersity of 0.299. Zeta potential measurements showed a charge of +32.2 mV for these nanoparticles.

Example 12c

WC-Bio-26b: 0.52 (0.75 DL-Arginine/0.25 L-Isoleucine)/Cerium

Into a 600 ml glass beaker containing a magnetic stir bar was introduced 500 ml of high purity (HP) water. A 1.613 gm quantity of DL-Arginine and 0.401 gm quantity of L-Isoleucine were dissolved in this volume. A 10.0 gm quantity of $Ce(NO_3)_3 \cdot 6(H_2O)$ was added, thereby forming a molar ratio of amino acids to cerium ion of 0.52. Then a 10 ml solution containing 1.2 gm of 50% $H_2O_2$ (0.75 molar ratio of $H_2O_2$ to cerium ion) was added slowly to the cerium, arginine and isoleucine solution mixture. The pH was further adjusted to about 2.0 by the addition of 1N $HNO_3$. The reaction product was then heated to 40° C. for 1 hour. The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.25 nm with a polydispersity of 0.283.

Example 12d

WC-Bio-26c: 0.4 (0.3 DL-Arginine/0.7 L-Isoleucine)/Cerium

Into a 600 ml glass beaker containing a magnetic stir bar was introduced 500 ml of high purity (HP) water. A 0.496 gm quantity of DL-Arginine and 0.863 gm quantity of L-Isoleucine were dissolved in this volume. A 10.0 gm quantity of $Ce(NO_3)_3 \cdot 6(H_2O)$ was added, thereby forming a molar ratio of amino acids to cerium ion of 0.4. Then a 10 ml solution containing 1.2 gm of 50% $H_2O_2$ (0.75 molar ratio of $H_2O_2$ to cerium ion) was added slowly to the cerium, arginine and isoleucine solution mixture. The pH was further adjusted to about 2.0 by the addition of 1N $HNO_3$. The reaction product was then heated to 40° C. for 1 hour. The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 14.85 nm with a polydispersity of 0.367.

Preparation of Nanoparticles with Cerium and Phenylalanine

Example 13

WC-Bio-25: 0.8 L-Phenylalanine/Cerium

Into a 600 ml glass beaker containing a magnetic stir bar was introduced 500 ml of high purity (HP) water. A 0.993 gm quantity of L-Phenylalanine was dissolved in this volume. A 5.0 gm quantity of $Ce(NO_3)_3 \cdot 6(H_2O)$ was added, thereby forming a molar ratio of phenylalanine to cerium ion of 0.8. Then a 10 ml solution containing 1.2 gm of 50% $H_2O_2$ (1.5 molar ratio of $H_2O_2$ to cerium ion) was added slowly to the cerium and phenylalanine solution mixture, and a pH of about 4.3 was recorded. The reaction product was then heated to 40° C. for 1 hour. The product dispersion was a clear yellow liquid that displayed a high degree of Tyndall scattering when illuminated with a low intensity LASER beam, indicating it contained well-dispersed colloidal particles. Particle size analysis by dynamic light scattering indicated a hydrodynamic diameter of 30.45 nm with a polydispersity of 0.183.

Preparation of Nanoparticles with Cerium and Methionine

Example 14

WC-Bio-21: 0.4 L-Methionine/Cerium

Into a 600 ml glass beaker containing a magnetic stir bar was introduced 500 ml of high purity (HP) water. A 0.993 gm quantity of L-Methionine was dissolved in this volume. A 5.0 gm quantity of $Ce(NO_3)_3 \cdot 6(H_2O)$ was added, thereby forming a molar ratio of ammethionineto cerium ion of 0.8. Then a 10 ml solution containing 1.2 gm of 50% $H_2O_2$ (1.5 molar ratio of $H_2O_2$ to cerium ion) was added slowly to the cerium and methionine solution mixture, and a pH of about 3.56 was recorded. The reaction product was then heated to 40° C. for 1 hour. The product dispersion was a clear orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 60.45 nm with a polydispersity of 0.2065.

Preparation of Nanoparticles with Cerium and Glycine

Example 15

WC-Bio-16: 0.8 Glycine/Cerium

Into a 600 ml glass beaker containing a magnetic stir bar was introduced 500 ml of high purity (HP) water. A 0.699 gm quantity of Glycine was dissolved in this volume. A 5.0 gm quantity of $Ce(NO_3)_3 \cdot 6(H_2O)$ was added, thereby forming a molar ratio of glycine to cerium ion of 0.8. Then a 10 ml solution containing 1.2 gm of 50% $H_2O_2$ (1.5 molar ratio of $H_2O_7$ to cerium ion) was added slowly to the cerium and glycine solution mixture, and a pH of about 4.0 was recorded. The reaction product was then heated to 40° C. for 1 hour. The product dispersion was a clear dark orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 73.35 nm with a polydispersity of 0.085.

Nanoparticle-Nucleic Acid Conjugate Formation

Various amounts of plasmid DNA or siRNA were combined with the aqueous amino acid stabilized cerium-containing nanoparticle dispersions and mixed for about 10 minutes in order to form conjugates.

The efficacy of binding DNA with the amino acid stabilized cerium-containing nanoparticles prepared in each of Examples 1b, 3a,3e, 3f,3h,3i,6a,6d, 12a, 12c and 12d was confirmed by both gel electrophoresis studies and YOYO-1 fluorescence studies of DNA condensation. Further analysis of zeta potentials confirmed that the nanoparticle-DNA conjugates were positively charged.

These positive DNA binding results were a marked improvement over those obtained with nanoceria particles stabilized by a combination of citric acid and ethylenediaminetetraacetic acid (EDTA), prepared as described in commonly assigned U.S. patent application Ser. No. 13/838,332, that are known to possess a significantly negative zeta potential in the range of about −20 mV to −30 mV. While not wishing to be bound by any particular theory, poor binding of citric acid/EDTA stabilized nanoceria to DNA may result from both substrates bearing an overall negative charge at physiological pH.

In summary, the inventors have discovered that cerium-containing nanoparticles prepared in the presence of the amino acid arginine or combinations of arginine/histidine, arginine/serine and arginine/isoleucine, and including an additional step of adjusting the pH to less than about 3, are surprisingly effective in binding with plasmid DNA to form conjugates.

Transfection Experiments

Transfections were performed on several transformed cell lines (COS, HeLa), using a standard transfection protocol as follows: various amounts of the nanoparticle-nucleic acid conjugates were added directly to cells in serum-free media for 4 hrs, with complete (serum-containing) media added back following 4 hrs, and then gene expression/function (plasmid DNA) or gene knockdown (siRNA) was measured at varying timepoints thereafter.

Tranfection studies on HeLa cells were performed using nanoparticle-DNA conjugates of arginine-stabilized cerium-containing nanoparticles of varying stabilizer to cerium molar ratios. In particular, at a 0.8:1 molar ratio of arginine to cerium (prepared in Example 1d), a transfection efficiency nearly two orders of magnitude greater than the non-conjugated control (cells+DNA) was observed.

Additional transfection studies involved the use of DNA conjugates with cerium-containing nanoparticles stabilized by a mixture of amino acids, including various molar ratios of combinations of arginine and histidine, arginine and serine, and arginine and isoleucine. In particular, transfection efficiency levels above controls were seen when using cerium-containing nanoparticle-DNA conjugates employing a 0.77 Arginine/0.23 Histidine mixture of stabilizers (prepared in Example 3e), and for a 0.8 Arginine/0.2 Histidine mixture (prepared in Example 3h).

Furthermore, enhanced gene silencing using specific siRNAs (e.g. GAPDH) was observed using siRNA conjugates with cerium-containing nanoparticles stabilized with either 0.77 Arginine/0.23 Histidine (prepared in Example 3e) or 0.7 Arginine/0.3 Serine (prepared in Example 6a).

While the invention has been described by reference to various specific embodiments, it should be understood that numerous changes may be made within the spirit and scope of the inventive concepts described. Accordingly, it is intended that the invention not be limited to the described embodiments, but will have full scope defined by the following claims.

What is claimed:

1. A process of making nanoparticles, comprising:
   forming a reaction mixture comprising a solution of cerous ion, an α-amino acid, an oxidant, and water, wherein the α-amino acid is a compound of formula H$_2$NCHRCOOH, wherein R is a side chain;
   adjusting said reaction mixture to a pH less than about 3; and
   heating or cooling said reaction mixture to a temperature in the range of about 0° C. to about 100° C. to form the nanoparticles and to directly form a dispersion of nanoparticles from the reaction mixture,
   wherein said nanoparticles have a hydrodynamic diameter of less than 100 nm.

2. The process according to claim 1, wherein said nanoparticles comprise crystalline or semi-crystalline material.

3. The process according to claim 1, wherein said oxidant is hydrogen peroxide.

4. A process of making a conjugate, comprising:
   contacting a nanoparticle formed according to the process of claim 1, with a biologically active agent.

5. The process of claim 4, wherein said nanoparticle comprises cerium oxide.

6. The process of claim 4, wherein said biologically active agent is comprised of ribonucleic acid, deoxyribonucleic acid, protein or lipid.

7. The process according to claim 1, wherein the α-amino acid is arginine, histidine, or lysine.

8. The process according to claim 1, wherein the α-amino acid is serine, threonine, asparagine, or glutamine.

9. The process according to claim 1, wherein the α-amino acid is aspartic acid or glutamic acid.

10. The process according to claim 1, wherein the α-amino acid is alanine, valine, isoleucine, leucine, methionine, phenylalanine, tyrosine, or tryptophan.

11. The process according to claim 1, wherein the α-amino acid is cysteine, selenocysteine, glycine, or proline.

12. The process according to claim 1, wherein the α-amino acid is selected from the group consisting of arginine, histidine, lysine, serine, threonine, asparagine, glutamine, aspartic acid, glutamic acid, alanine, valine, isoleucine, leucine, methionine, phenylalanine, tyrosine, tryptophan, cysteine, selenocysteine, glycine, proline, and mixtures thereof.

13. The process according to claim 4, wherein the α-amino acid is arginine, histidine, or lysine.

14. The process according to claim 4, wherein the α-amino acid is serine, threonine, asparagine, or glutamine.

15. The process according to claim 4, wherein the α-amino acid is aspartic acid or glutamic acid.

16. The process according to claim 4, wherein the α-amino acid is alanine, valine, isoleucine, leucine, methionine, phenylalanine, tyrosine, or tryptophan.

17. The process according to claim 4, wherein the α-amino acid is cysteine, selenocysteine, glycine, or proline.

18. The process according to claim 4, wherein the α-amino acid is selected from the group consisting of arginine, histidine, lysine, serine, threonine, asparagine, glutamine, aspartic acid, glutamic acid, alanine, valine, isoleucine, leucine, methionine, phenylalanine, tyrosine, tryptophan, cysteine, selenocysteine, glycine, proline, and mixtures thereof.

* * * * *